(12) United States Patent
Kelman et al.

(10) Patent No.: US 11,298,189 B2
(45) Date of Patent: Apr. 12, 2022

(54) PROSTHESIS GUIDE COMPRISING PATIENT-MATCHED FEATURES

(71) Applicant: Smith & Nephew, Inc., Memphis, TN (US)

(72) Inventors: David C. Kelman, Somerville, TN (US); Richard D. Lambert, Collierville, TN (US); Craig Della Valle, Chicago, IL (US); Sachin P. Budhabhatti, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 269 days.

(21) Appl. No.: 16/790,332

(22) Filed: Feb. 13, 2020

(65) Prior Publication Data

US 2020/0179134 A1 Jun. 11, 2020

Related U.S. Application Data

(60) Continuation of application No. 15/906,543, filed on Feb. 27, 2018, now Pat. No. 10,568,746, which is a division of application No. 14/123,492, filed as application No. PCT/US2012/040164 on May 31, 2012, now Pat. No. 9,956,089.

(Continued)

(51) Int. Cl.
*A61B 34/10* (2016.01)
*A61F 2/46* (2006.01)
*A61F 2/30* (2006.01)

(52) U.S. Cl.
CPC ............ *A61B 34/10* (2016.02); *A61F 2/4609* (2013.01); *A61F 2/30942* (2013.01); *A61F 2002/30576* (2013.01); *A61F 2002/30784* (2013.01)

(58) Field of Classification Search
CPC ............................. A61B 34/10; A61F 2/30942
See application file for complete search history.

(56) References Cited

U.S. PATENT DOCUMENTS 6,214,014 B1 * 4/2001 McGann ............... A61F 2/4657
606/102
6,224,373 B1 * 5/2001 Lee ........................ A61B 6/505
433/172

(Continued)

FOREIGN PATENT DOCUMENTS

CN 101711695 A 5/2010
DE 102008053566 A1 6/2009

(Continued)

OTHER PUBLICATIONS

Australia Examination Report No. 1 for AU 2012262215 dated Dec. 16, 2015 (4 pages).

(Continued)

*Primary Examiner* — Christian A Sevilla
(74) *Attorney, Agent, or Firm* — Kacvinsky Daisak Bluni PLLC

(57) ABSTRACT

Systems, devices and methods for guiding placement, orientation, and fixation of an orthopedic implant. Examples include a surgical guide having a first surface structured to fit within a prosthetic cup, at least one guide hole through the first surface, and an alignment structure having a contour formed from data indicative of the patient anatomy. The contour of the alignment surface is complementary to a portion of the patient anatomy in a unique orientation that aligns the guide hole with tissue suitable for receiving a fastener. The alignment structure preferably includes an arm with a first end coupled to a rim of the guide and a second end coupled to the contour. In certain implementations, the guide includes a plurality of alignment structures. Further disclosed are methods of making and using a surgical guide for aligning an orthopedic implant.

18 Claims, 24 Drawing Sheets

Related U.S. Application Data

(60) Provisional application No. 61/561,619, filed on Nov. 18, 2011, provisional application No. 61/493,260, filed on Jun. 3, 2011.

(56) References Cited

U.S. PATENT DOCUMENTS

| | | | |
|---|---|---|---|
| 7,291,177 B2 | 11/2007 | Gibbs | |
| 8,551,181 B2* | 10/2013 | Meridew | A61F 2/30734 623/22.28 |
| 2001/0007919 A1* | 7/2001 | Shahidi | A61B 5/064 600/427 |
| 2001/0033682 A1* | 10/2001 | Robar | A61N 5/1048 382/132 |
| 2003/0105529 A1 | 6/2003 | Synder et al. | |
| 2003/0171818 A1* | 9/2003 | Lewallen | A61F 2/30767 623/22.22 |
| 2004/0073225 A1 | 4/2004 | Subba Rao | |
| 2005/0148843 A1 | 7/2005 | Roose | |
| 2005/0197814 A1* | 9/2005 | Aram | A61F 2/38 703/11 |
| 2006/0058883 A1* | 3/2006 | Aram | A61F 2/38 623/20.15 |
| 2006/0161167 A1* | 7/2006 | Myers | A61B 17/1746 606/91 |
| 2009/0012526 A1 | 1/2009 | Fletcher | |
| 2009/0088753 A1* | 4/2009 | Aram | A61B 17/157 606/79 |
| 2011/0093086 A1 | 4/2011 | Witt et al. | |
| 2011/0190775 A1 | 8/2011 | Ure | |
| 2012/0303035 A1 | 11/2012 | Geebelen | |
| 2013/0211407 A1* | 8/2013 | Geebelen | A61B 17/1742 606/80 |
| 2014/0324181 A1* | 10/2014 | Bergin | A61F 2/4609 623/22.12 |
| 2016/0184109 A1* | 6/2016 | Davenport | A61F 2/4609 606/91 |

FOREIGN PATENT DOCUMENTS

| | | |
|---|---|---|
| EP | 2519165 B1 | 2/2015 |
| EP | 2168507 B1 | 4/2016 |
| JP | H09511668 A | 11/1997 |
| JP | 2009056341 A | 3/2009 |
| JP | 2010131398 A | 6/2010 |
| JP | 2011512925 A | 4/2011 |
| KR | 20050042228 A | 5/2005 |
| WO | 2010124164 A1 | 10/2010 |
| WO | 2011060536 A1 | 5/2011 |

OTHER PUBLICATIONS

Canadian Office Action for CA 2837872 dated May 11, 2018 (4 pages).
Chinese Office Action for CN 201280038669.X dated Aug. 28, 2015 (15 pages).
Chinese Search Report for CN 201280038669.X dated Aug. 19, 2015 (5 pages).
Chinese Second Office Action for CN 201280038669.X dated Jul. 4, 2016 (3 pages).
Chinese Supplemental Search Report for CN 201280038669.X dated Mar. 14, 2017 (5 pages).
Chinese Third Office Action for CN 201280038669.X dated Mar. 23, 2017 (16 pages).
Indian Examination Report for IN 10370/DELNP/2013 dated Dec. 24, 2019 (9 pages).
International Search Report and Written Opinion for PCT/US2012/040164 dated Jan. 29, 2013.
Japanese Office Action for JP 2004513688 dated Dec. 19, 2016 (4 pages).
Japanese Office Action for JP2014513688 dated Mar. 7, 2016 (11 pages).
Russian Office Action for RU 2013157034 dated Apr. 12, 2016 (6 pages).

* cited by examiner

PROSTHESIS GUIDE COMPRISING PATIENT-MATCHED FEATURES

RELATED APPLICATIONS

The present application is a continuation application of U.S. patent application Ser. No. 15/906,543 filed Feb. 27, 2018 and entitled "Prosthesis Guide Comprising Patient-Matched Features," which is a divisional of U.S. patent application Ser. No. 14/123,492 filed Dec. 2, 2013, which is a U.S. National Stage filing under 35 U.S.C. § 371 of International PCT Application No. PCT/US2012/040164 filed May 31, 2012, which claims the benefit of U.S. Provisional Patent Application No. 61/493,260 filed Jun. 3, 2011, and U.S. Provisional Patent Application No. 61/561,619 filed Nov. 18, 2011, each of which are hereby incorporated herein by reference in their entireties.

RELATED FIELDS

The disclosure relates generally to surgery and more particularly to orthopedic instruments for use in bone reparation.

BACKGROUND

Joints undergo degenerative changes for a variety of reasons. When joint degeneration becomes advanced or irreversible, it may become necessary to replace the natural joint with a prosthetic joint. Artificial implants, including hip joints, shoulder joints, and knee joints are widely used in orthopedic surgery. Specifically, hip joint prostheses are common. The human hip joint acts mechanically as a ball and socket joint, where the ball-shaped head of the femur is positioned within the socket-shaped acetabulum of the pelvis. Various degenerative diseases and injuries may require replacement of all or a portion of a hip or other joints using prosthetic implants constructed of metals, ceramics, plastics, or other synthetic materials.

A "joint revision" refers to a surgery wherein a surgeon removes an existing orthopedic implant, such as a knee or hip prosthesis, and replaces it with a revision implant. Revision surgeries may become necessary due to degeneration of bone over time or advancement of a degenerative disease. For example, bone is often lost around the rim of the acetabulum, and this may provide less rim coverage to securely place a prosthetic cup or to place bone screws.

In joint restoration and revision surgeries, the patient's anatomy surrounding the joint is severely degraded or damaged to the point where accurate navigation of the surgical instruments and proper placement of implants becomes a significant challenge that can negatively impact surgical outcomes. For example, a surgeon may be unable to locate and identify anatomical reference points that are needed to perform the surgery. It may also be difficult for the surgeon to locate and identify sensitive areas, such as blood vessels or nerves that should be avoided during surgery. For example, the surgeon may need to identify and locate portions of the patient's anatomy that are of sufficient quality to accept mechanical fasteners, such as bone screws, and thereby secure and stabilize the implant, while avoiding blood vessels, nerve, or other sensitive areas. Improved, patient-matched surgical guides that align a prosthetic implant and direct placement of fasteners to suitable areas of anatomy may help surgeons improve surgical outcomes.

SUMMARY

Disclosed herein are systems, devices, and methods for guiding placement, orientation, and fixation of an orthopedic implant. Examples include a patient-matched surgical guide having a first surface structured to fit within a prosthetic cup, at least one guide hole through the first surface, and an alignment structure having a contour formed from data indicative of the patient's anatomy. In certain implementations, the first surface is substantially hemispherical to fit within a prosthetic cup. The contour of the alignment structure is complementary to a portion of the patient anatomy in a unique orientation that aligns the cup in relation to the acetabulum and aligns the guide hole with tissue suitable for receiving a fastener. In certain embodiments, the guide has a rim along the first surface. The alignment structure preferably includes an arm with a first end coupled to the rim of the guide and a second end coupled to the contour. In certain implementations, the guide includes a plurality of alignment structures. In certain implementations, the rim is substantially elliptical.

In general, the surgical guide is used with a prosthetic cup or other orthopedic device to guide the device to an appropriate position and secure the device to bone suitable for receiving a fastener, as determined in a pre-operative plan based on patient data. In certain embodiments, the guide has a keying structure to align the guide relative to a prosthetic cup. The keying structure may temporarily fix the guide and cup together for implanting the cup at the surgical site, such as the acetabulum. Example keying structures include protrusions, dimples, fins, channels, slots, grooves, tapers, and pins. Certain implementations include a central aperture in an apical region of the guide.

In certain approaches, systems, devices, and methods are provided for guiding placement, orientation, and fixation of an orthopedic implant. Examples include a patient-matched surgical guide having a first surface structured to fit within a prosthetic cup and an alignment structure having a contour formed from data indicative of the patient's anatomy. In certain implementations, the first surface is substantially hemispherical to fit within a prosthetic cup. The contour of the alignment structure is complementary to a portion of the patient anatomy in a unique orientation that aligns the cup in relation to the acetabulum. In certain embodiments, the guide has a rim along the first surface. The alignment structure preferably includes an arm with a first end coupled to the rim of the guide and a second end coupled to the contour. In certain implementations, the guide includes a plurality of alignment structures. In certain implementations, the rim is substantially elliptical.

In another aspect, methods are provided for making a surgical guide that aligns a prosthetic cup. In practice, imaging data of the patient's anatomy is acquired, the data is used to develop a plan before the surgery for placing a prosthetic cup or other orthopedic device and inserting fasteners. The data is used to design a customized, patient-matched guide for placing the cup and fasteners according to the pre-operative plan, whereupon the guide is manufactured used for the specific patient to place the prosthetic cup and fasteners.

Methods for making a surgical guide include one or more of the steps of acquiring imaging data of a portion of a patient's anatomy, processing the imaging data, identifying at least one suitable location on the patient's anatomy for placement of a fastener, identifying an anatomical alignment surface on the patient's anatomy, forming a first surface of the guide structured to fit within a prosthetic cup, forming a hole through the first surface that is substantially aligned with the identified suitable location, and forming a patient-matched surface with a contour that is complementary to the identified anatomical alignment surface. In certain embodiments, methods include identifying a desired position and orientation of an orthopedic cup. For example, the method may include defining a target abduction angle and a target anteversion angle for the orientation of the cup. In certain embodiments, the method includes forming a plurality of guide holes through the first surface, wherein each hole is aligned with an identified suitable location for placement of a fastener. Certain embodiments include forming a plurality of patient-matched surfaces.

Further disclosed herein are systems, devices, and methods for using an orthopedic guide to place an orthopedic implant, such as a prosthetic cup. In certain embodiments, methods include providing a first cup, such as a prosthetic cup, having a plurality of apertures, providing a second cup or guide having at least one guide hole and a guide surface with a contour complementary to a portion of a patient's anatomy, inserting the second cup into the first cup to form an assembly, and aligning the at least one guide hole of the second cup with at least one of the plurality of apertures of the first cup. The methods may further comprise inserting the assembled first and second cups into a surgical site and mating the guide surface to the portion of the patient's anatomy in a predetermined orientation. In certain embodiments, the method of using a surgical guide with an implant includes covering at least one of the plurality of apertures in the first cup with the second cup. The implant may be secured to the bone at the surgical site by providing a fastener, such as a screw, inserting the fastener through the at least one guide hole, and inserting the fastener into the bone. The second cup, or guide, is preferably removed from the implant and surgical site.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, devices, and methods described herein, certain illustrative embodiments will be described. Although the embodiments and features described herein are specifically described for use in connection with orthopedic hip procedures, it will be understood that all the components, connection mechanisms, adjustable systems, manufacturing methods, and other features outlined below may be combined with one another in any suitable manner and may be adapted and applied to devices and implants to be used in other surgical procedures, including, but not limited to hip arthroplasty, knee arthroplasty, spine arthroplasty, cranio-maxillofacial surgical procedures, shoulder arthroplasty, as well as foot, ankle, hand, and other extremity procedures.

Disclosed herein are systems, devices, and methods for guiding placement, orientation, and fixation of an orthopedic implant. Examples include a patient-matched surgical guide having a first surface structured to fit within a prosthetic cup, at least one guide hole through the first surface, and an alignment structure having a contour formed from data indicative of the patient's anatomy. In certain implementations, the first surface is substantially hemispherical to fit within a prosthetic cup. The contour of the alignment structure is complementary to a portion of the patient anatomy in a unique orientation that aligns the cup in relation to the acetabulum and aligns the guide hole with tissue suitable for receiving a fastener. In certain embodiments, the guide has a rim along the first surface. The alignment structure preferably includes an arm with a first end coupled to the rim of the guide and a second end coupled to the contour. In certain implementations, the guide includes a plurality of alignment structures. In another aspect, methods are provided for making a surgical guide that aligns a prosthetic cup or other prosthetic device, including developing a pre-operative plan based on patient data and forming a patient-matched alignment structure on the surgical guide. Further disclosed herein are systems, devices, and methods for using an orthopedic guide to place an orthopedic device or implant, such as a prosthetic cup.

Figure 1:
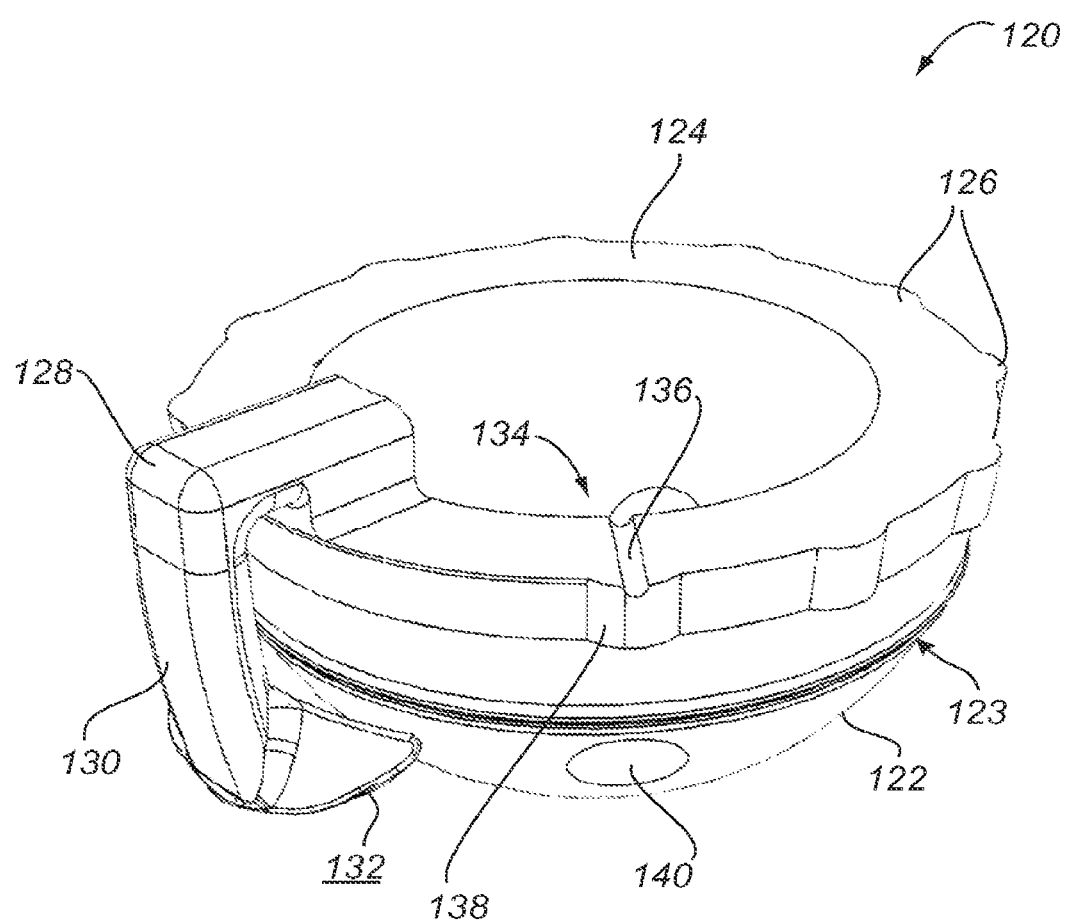
FIGS. 1-3 show a surgical guide with a patient-matched alignment structure for placement of an orthopedic prosthesis.
Figure 2:
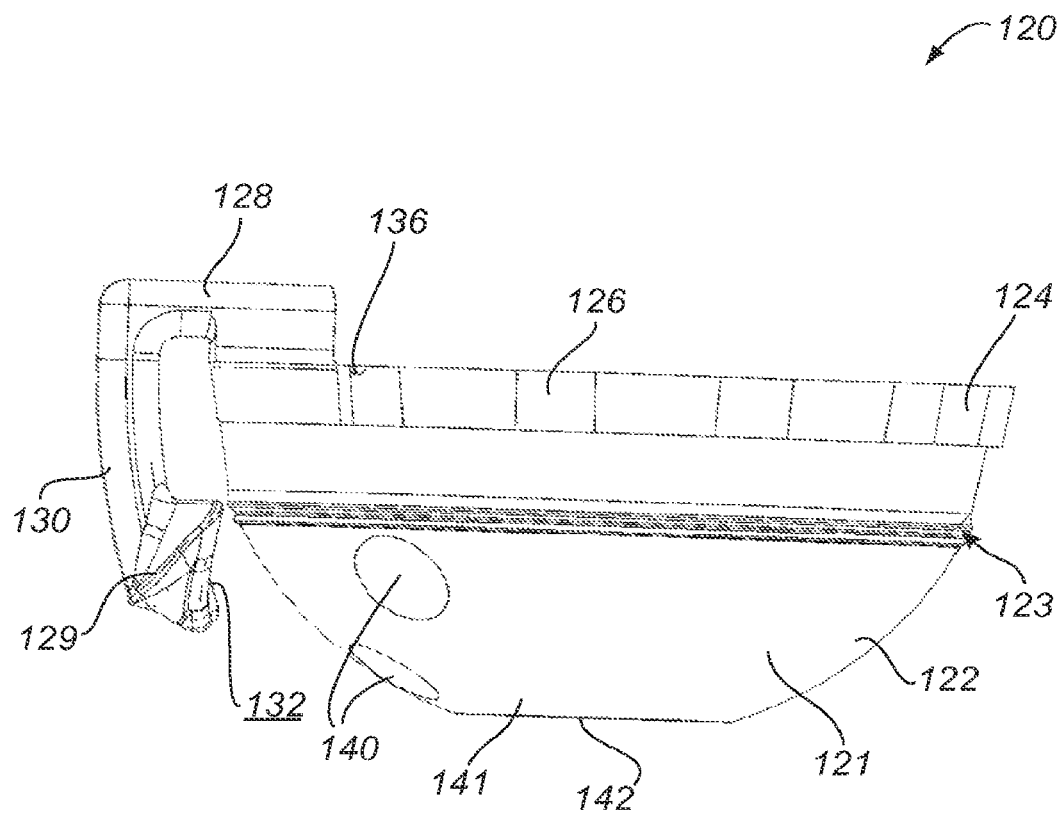
Figure 3:
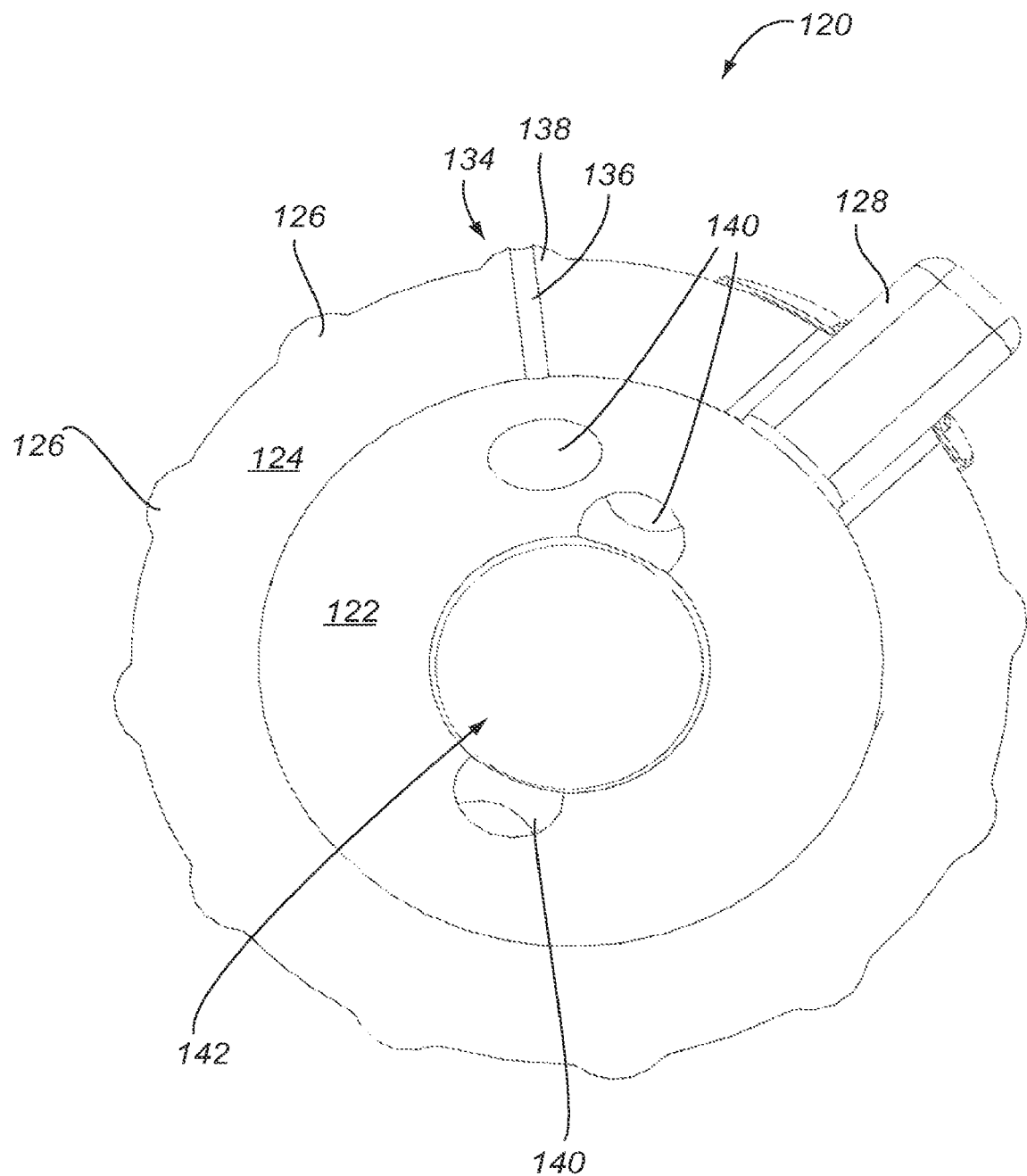

FIGS. 1-3 show a surgical guide 120 configured for use in an orthopedic repair procedure. Specifically, FIG. 1 depicts an upper perspective view of the guide 120, FIG. 2 depicts a side perspective view of the guide 120, and FIG. 3 depicts a top perspective view of the guide 120. The guide 120 includes an alignment structure 128 for placement and fixation of an orthopedic prosthesis in a predetermined orientation. In certain embodiments, alignment structure 128 includes an arm 130 with a patient-matched surface 132 structured to form a complementary fit with a specific portion of the patient anatomy, such as a patient's acetabulum, in a unique orientation to align the cup to the acetabulum as determined in a pre-operative plan based on patient data, as described herein. The guide 120 is also used to align guide holes for fasteners with tissue suitable for receiving a fastener.

In certain embodiments, the guide 120 includes a cup portion 122 and a rim portion 124. The cup portion 122 includes at least one hole 140 for receiving and directing a fastener, such as a screw. As shown, the cup portion 122 has a substantially hemispherical shape. In certain embodiments, the rim 124 is substantially elliptical. The position of the hole 140 aligns with bone or tissue within the patient's anatomy suitable for retaining a fastener, such as a screw. More than one hole 140 may be provided if there is more than one area of suitable anatomy. Areas of suitable anatomy are identified based on patient-specific data, as will be described herein. To retain a fastener or screw, the bone or other tissue must have sufficient size (e.g., area and volume), density, and strength. Further, suitable locations for a fastener would preferably avoid sensitive areas, such as blood vessels and nerves. In practice, the location, dimensions, and orientation of the hole 140 are determined in a pre-operative plan based on patient data, as described herein. In certain embodiments, patient-matched data is used to determine the size, length, or type of fastener to use. These parameters, in turn, affect the size, location, and orientation of hole 140 provided on guide 120. For example, if there is a particularly large area of suitable anatomy in one location, a larger fastener, which would require a larger hole 140, may be used for improved fixation. In certain embodiments, no holes are included on the guide 120. In certain approaches, the holes may not be necessary because the prosthesis or cup may be secured to the patient anatomy without screws. For example, the cup may be secured by a tight fit with thee acetabulum or with bone cement, or the surgeon may decide to place screws without the guide.

Figure 4:
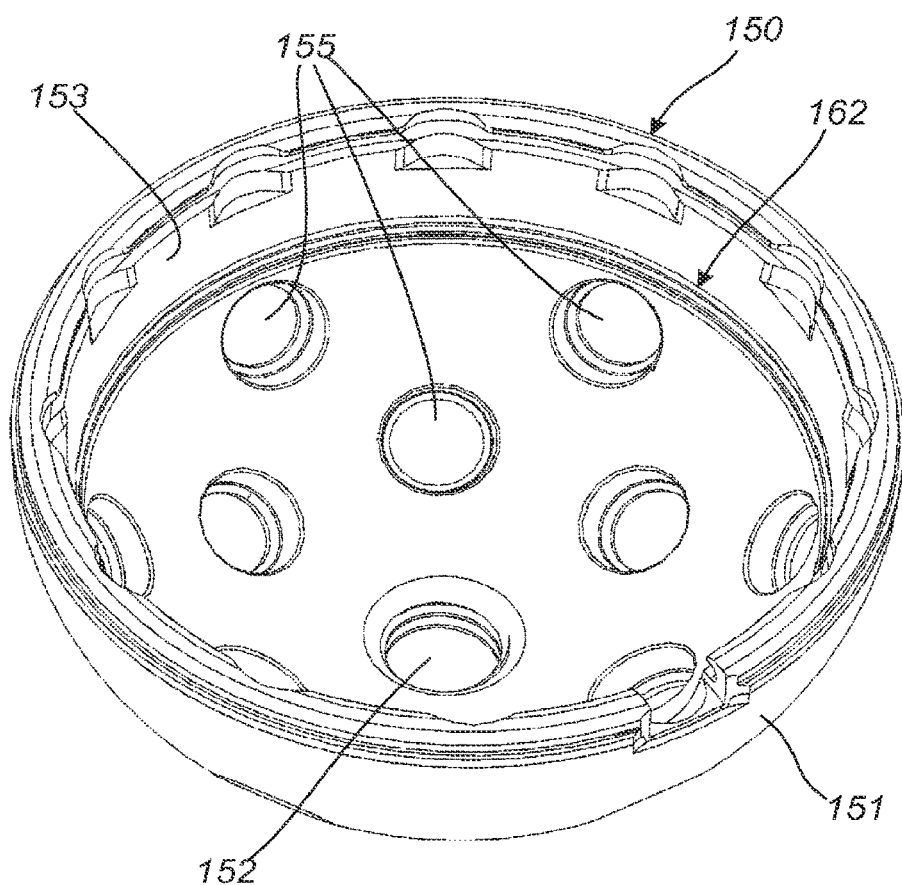
FIG. 4 shows a prosthesis cup for use with the surgical guide depicted in FIG. 1-3.
Figure 5:
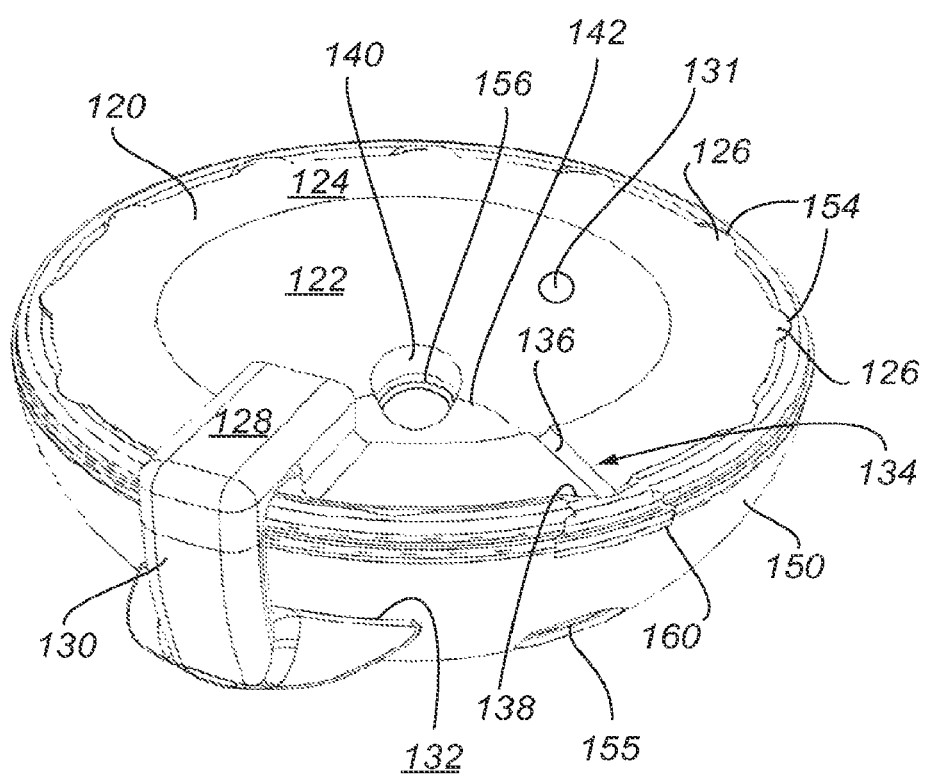
FIGS. 5 and 6 depict the guide of FIGS. 1-3 inserted within the prosthesis of FIG. 4.
Figure 6:
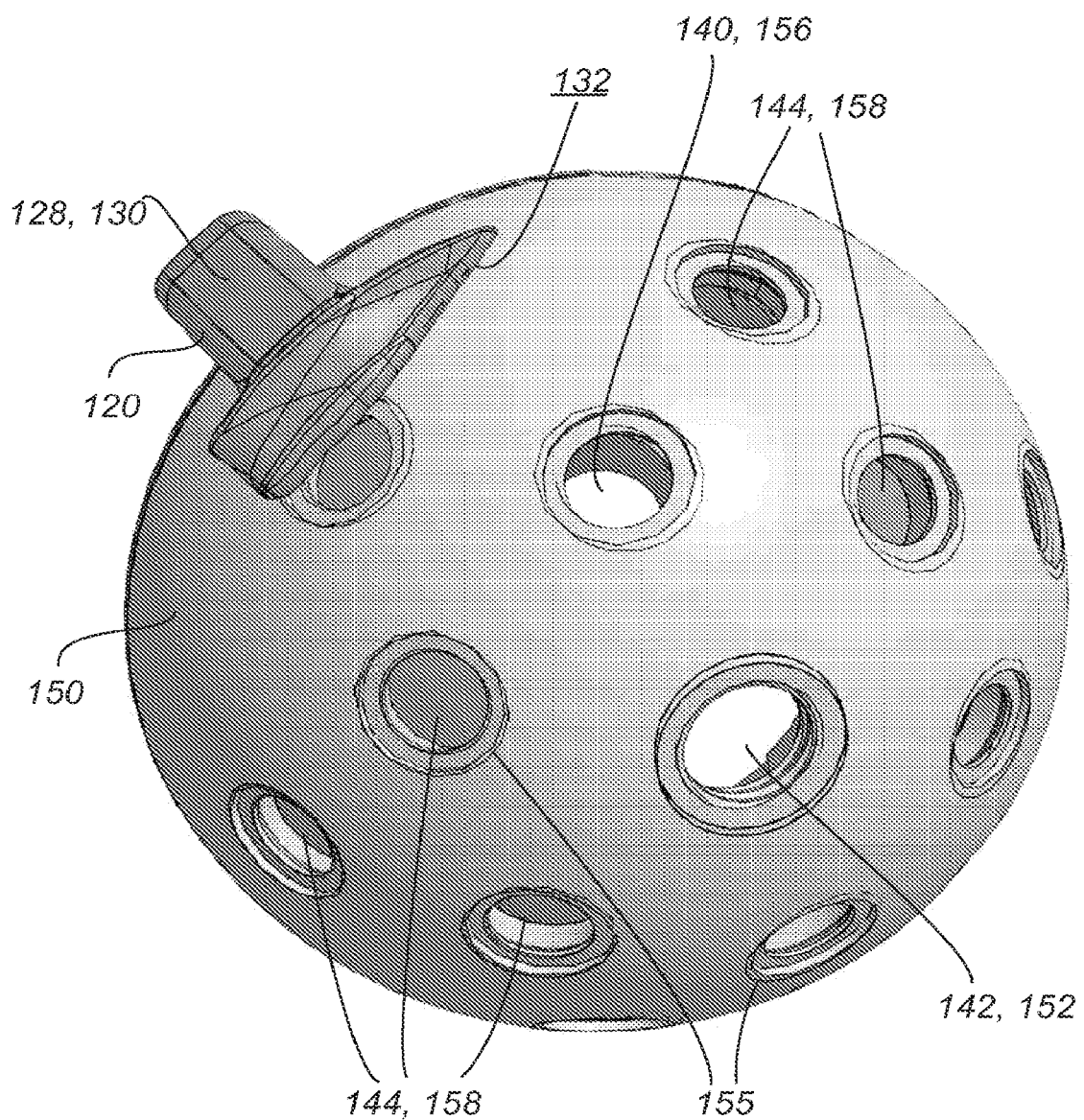

The guide 120 directs placement and fixation of a prosthesis, such as prosthetic cup 150 depicted in FIG. 4. In certain implementations, the prosthetic cup 150 is a standard acetabular cup, for which the guide 120 provides customized placement, orientation, and fixation for a specific patient. In alternative embodiments, the prosthetic cup is a customized device based on patient-matched data. In practice, as shown in FIGS. 5 and 6, the guide 120 and cup 150 are configured together by inserting guide 120 within the prosthetic cup 150 to guide the placement of the cup 150 into a desired position and orientation within the patient's anatomy. The cup portion 122 of the guide 120 has a substantially hemispherical shape and fits within the cup 150, with the outer surface 121 of the cup portion 122 coupling with the inner surface 153 of the cup 150. When so configured and placed, the cup 150 is positioned to fit next to the applicable anatomy and the guide 120 overlays the cup 150.

The guide 120 is also configured to allow the surgeon to install the cup 150 while aligned at the proper anatomic location, and thereafter be removed. To provide this function, one or more drill holes are provided in the guide 120. As shown, the prosthetic cup 150 includes several pre-drilled holes 155. The guide 120 may be used with standard prosthetic cup or a customized prosthetic cup. In the case of a standard acetabular cup, the location and quantity of holes 155 are standard standardized. In the case of a customized acetabular cup, the location and quantity of holes 155 are based on patient-specific data. A customized acetabular cup may also have other patient-specific features, such as patient-matched surfaces that complement the anatomy of a patient.

When the guide 120 is placed within the prosthetic cup 150, the hole 140 of the guide 120 aligns with a hole 155 of the prosthetic cup 150. This configuration exposes a hole 155 of the prosthetic cup 150 that corresponds to an area of suitable anatomy. For example, FIG. 6 shows a bottom view of a guide 120 inserted within prosthetic cup 150, with open hole 156 comprising a hole 155 of the prosthetic cup 150 and a hole 140 of the guide 120. In certain embodiments, the guide 120 includes a plurality of holes 140 that align with a plurality of holes 155 of the cup 150, wherein each hole 140 corresponds to an area of suitable anatomy. This configuration allows the surgeon to easily identify areas of suitable anatomy for placement of a fastener. This surgeon may choose to use one or more of the open holes 156 for placement of a fastener. FIG. 6 also shows covered holes 158 that comprise a hole 155 of the prosthetic cup 150 that is covered by a solid portion 144 of the guide 120. Covered holes 158 are unavailable for use with a fastener, thus the surgeon is prevented from drilling into an area of unsuitable anatomy.

In the particular embodiment shown in FIGS. 5 and 6, the cup portion 122 of the guide 120 is provided with a central aperture 142 that corresponds to a central hole 152 in the prosthetic cup 150. As seen, for example, in FIG. 2, the central aperture is located at the apical region 141 of the hemispherical cup portion 122 of the guide 120. The central aperture 142 in the guide 120 exposes the central hole 152 of the prosthetic cup 150 for coupling with an orthopedic instrument, such as an impactor. The central hole 152 may be provided with threads or other structures to couple the prosthetic cup 150 to the surgical instrument during surgery.

In certain embodiments, the guide 120 is temporarily affixed to the prosthetic cup 150 prior to installation, for example, to align guide 120 within cup 150 to form open holes 156 and covered holes 158. Temporarily locking the guide 120 to the prosthetic cup 150 provides the advantage of allowing placement of the guide and the prosthesis together as an assembled unit. Temporary locking can also prevent axial, rotational, or other movement of the guide 120 relative to the prosthetic cup 150 that would cause misalignment when placing the assembled unit at the surgical site (e.g., acetabulum). The temporary fixation may be done by one or more temporary fixation structures configured within the implant (e.g., the acetabular replacement cup), the guide, or both. Examples of temporary fixation structures are described in FIGS. 1-14.

Additional components may be added for further stability, if desired. For example, in the embodiments depicted in FIGS. 1-4, the guide 120 includes one or more circumferential bumps 123 that seat in one or more circumferential grooves 162 of the prosthetic cup 150. Similar bumps 123 and grooves 162 are disclosed in U.S. patent application Ser. No. 12/293,705 (Publication No. 2011/0009975), which is herein incorporated by reference in its entirety. When the guide 120 is placed in the cup 150, the bumps 123 fit into the grooves 162. In certain embodiments, guide 120 has a "snap fit" connection within the cup 150 such that the user (e.g., surgeon or technician) can feel or hear a snap or click when the bumps 123 of the guide 120 are properly positioned within the grooves 162 of the cup 150. When so configured and placed, the guide 120 can be rotated within the cup 150 to align the holes 140 of the guide 120 with the holes 155 of the cup 150 to form open holes 156 before placing the assembly (guide 120 and cup 150) at the surgical site. In certain implementations, the fit of bumps 123 within grooves 162 is tight and provides sufficient frictional resistance so that the guide 120 does not freely rotate within the cup 150, but can be rotated only with sufficient, intentional force. In alternative embodiments, the bumps 123 fit into the grooves 162 in a single, unique position that aligns the holes guide 120 within the cup 150 to form open holes 156 and covered holes 158. For example, the bumps 123 and 162 may extend around only a portion of the circumference of the guide 120 and cup 150. In certain embodiments, the guide 120 has grooves and the cup 150 has bumps.

In certain embodiments, the guide 120 includes protrusions 126 around the circumference of the rim portion 124. As seen in FIG. 5, the protrusions 126 engage and interlock with dimples 154 that are provided around the circumference of the prosthetic cup 150. The engagement of the protrusions 126 and the dimples 154 aligns the hole 140 of the guide 120 with a hole 155 of the cup 150 in a predetermined orientation to form an open hole 156. An individual protrusion 126 and dimple 154 extends around a portion, not the entirety, of the circumference of the guide 120 and cup 150. The protrusions 126 extend from the rim 124 to fit within dimples 154 thereby providing a temporary fixed relationship between the protrusions 126 and the dimples 154 to prevent rotation of the guide 120 within the prosthetic cup 150. The plurality of protrusions 126 and plurality of dimples 154 depicted in FIG. 5 are spaced evenly around the rim 124 of the guide and the circumference of the prosthetic cup 150. In preferred embodiments, any individual protrusion 126 can engage any individual dimple 154 for appropriate alignment of the guide 120 and cup 150. Although the guide 120 engages the cup 150 in a plurality of positions, in each position, the hole 150 of the guide 120 is aligned with an appropriate hole 155 of the cup 150 to faun an open hole 156. Although FIG. 5 depicts evenly spaced protrusions 126 and dimples 154, alternative, uneven spacing may also be used to provide a lock-and-key fit of the guide 120 in the prosthetic cup 150 in a single engagement position. For example, a first subset of protrusions and corresponding dimples may have closer spacing than a second subset of protrusions and corresponding dimples. The guide 120 would then fit within the cup 150 only by matching the first subset of protrusions with the corresponding first subset of dimples and by matching the second subset of protrusions with the corresponding second subset of dimples. In certain embodiments, the guide 120 has one protrusion 126 and cup 150 has one dimple 154 to provide a single engagement position. In certain embodiments, the protrusions 126 and dimples 154 have other shapes, for example, square or triangular.

In certain embodiments the guide 120 is provided with a prosthesis keying structure 134 that comprises a projection 138 and a slot 136 that are configured to fit securely together when the guide 120 and cup 150 are aligned in the proper, pre-determined orientation. In use, the surgeon aligns the slot 136 with the keying structure 160 on the prosthetic cup 150 by inserting the projection 138 into the keying structure 160. The coupling of the keying structures 134, 160 orients the prosthetic cup 150 relative to the guide 120 in a predetermined orientation. Specifically, the holes 140 of the guide 120 align with the corresponding holes 155 of the prosthetic cup 150 to provide open holes 156 that align with predetermined areas of suitable anatomy. The interlocking of keying structures 134, 160 providing a temporary fixed relationship between the keying structures 134, 160 to prevent rotation of the guide 120 within the prosthetic cup 150. The keying structures may have other forms. For example, the keying structures may comprise square or triangular shaped protrusions and dimples that can only engage with a specific, corresponding shape. In use, the surgeon or other user verifies by sight or touch that the hole 140 of the guide 120 aligns with a hole 155 in the prosthetic cup 150. In embodiments comprising a plurality of holes 140, each hole 140 in the guide 120 is aligned with a hole 155 in the cup 150.

Figure 7:
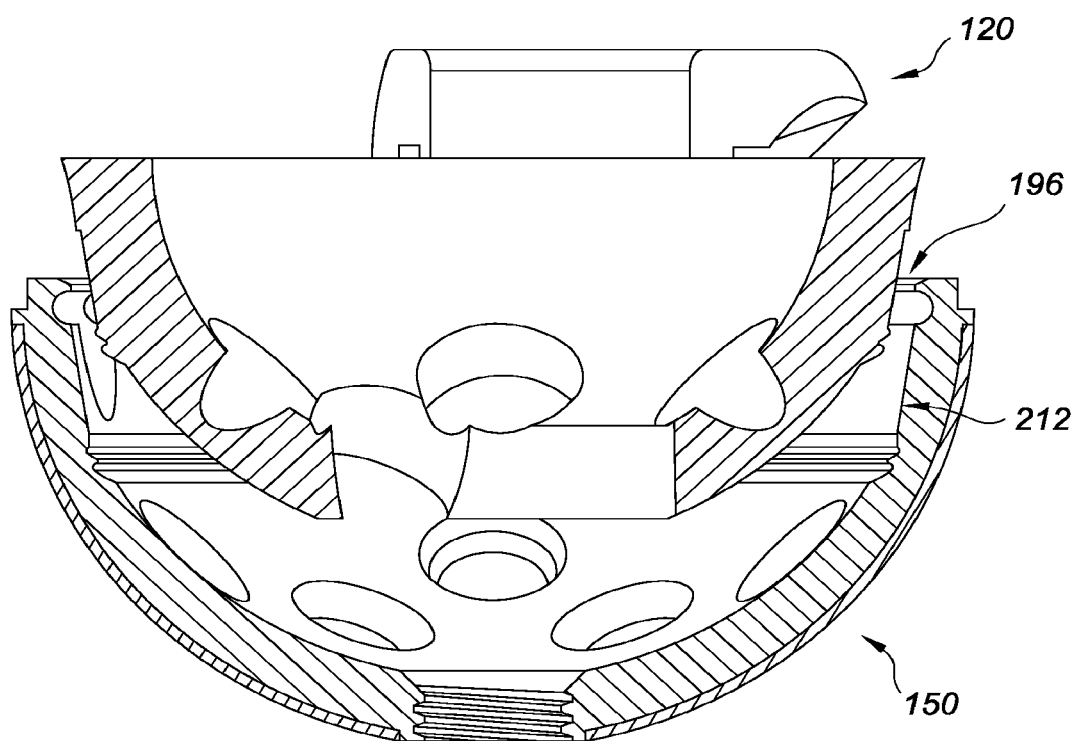
FIG. 7 shows a taper lock for temporary fixation of a guide and prosthesis.

FIG. 7 illustrates a cross-section of an embodiment with a tapered fit for locking the guide 120 to the prosthetic cup 150. The guide 120 has a first taper 196 and the prosthetic cup 150 has a second taper 212. When the guide 120 is inserted within the cup 150, the first taper 196 and second taper 212 engage in a tight fit to provide a locked position of the guide 120 within the cup 150. In practice, second taper 212 is slightly narrower than the first taper 196 so that the fit between the first taper 196 and second taper 212 becomes increasingly tight as the guide 120 is inserted further into the cup 150. In certain embodiments, the first taper 196 and second taper 212 are conical tapers. Alternatively, the taper interface of first taper 196 and second taper 212 may be a self-locking Morse taper.

Figure 8:
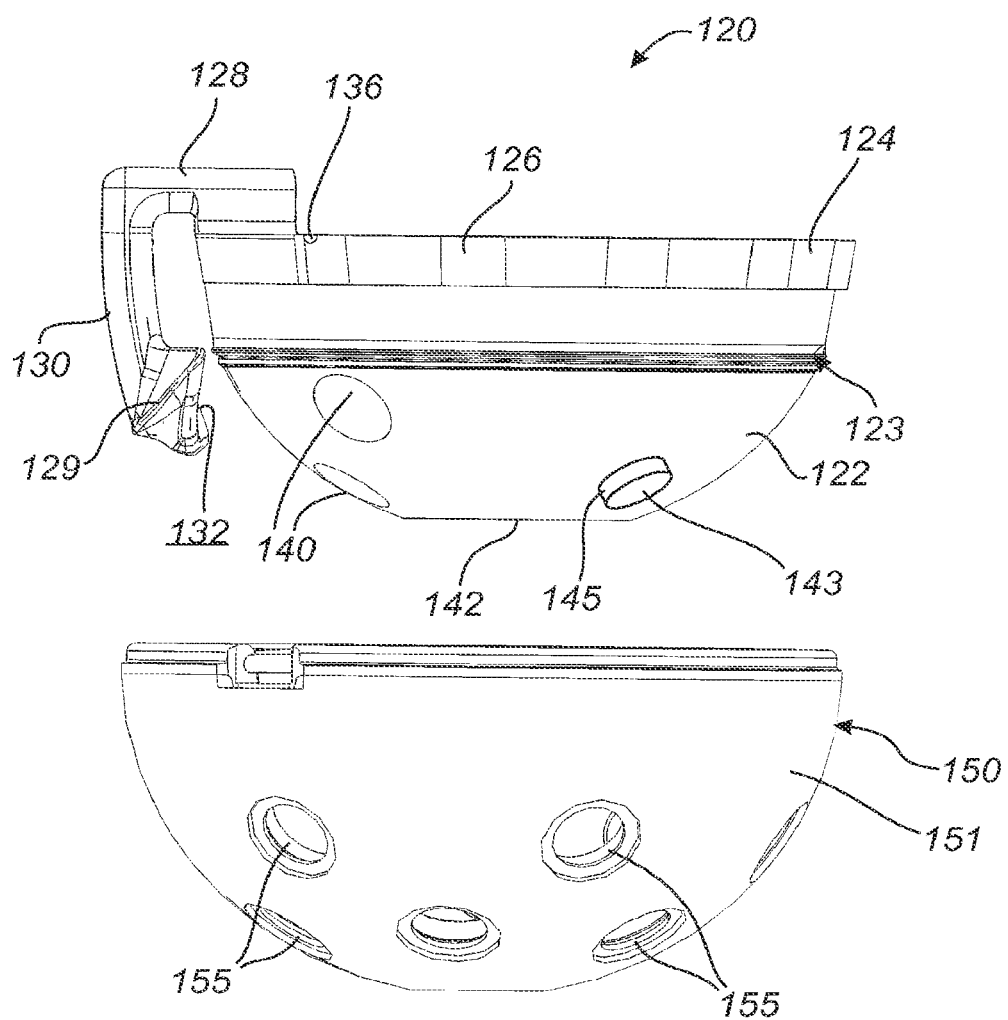
FIGS. 8 and 9 show a guide with an alignment plug for temporary fixation with a prosthesis.
Figure 9:
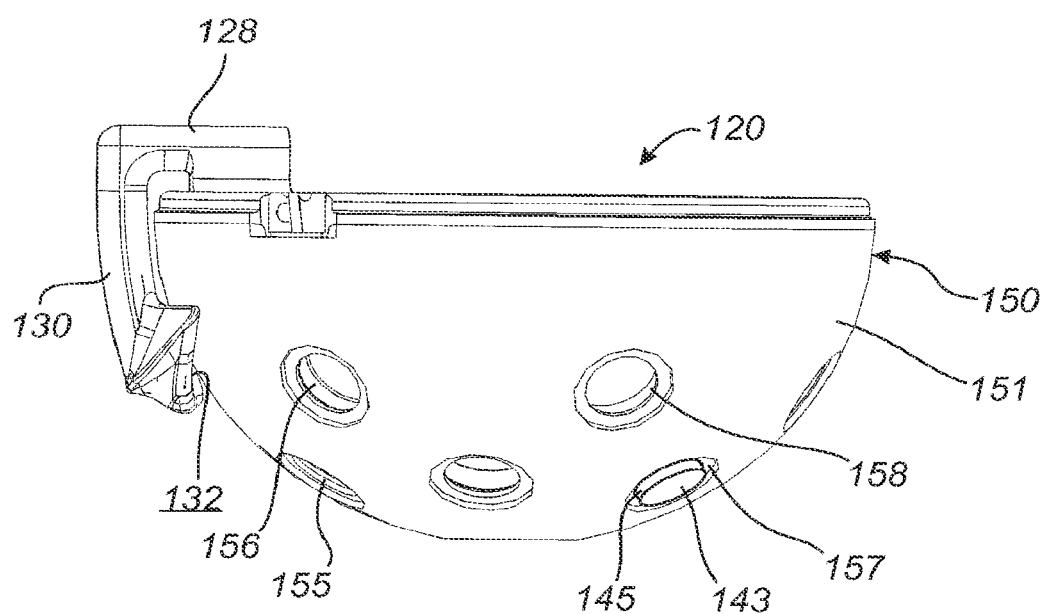

FIG. 8 depicts a guide 120 with an alignment plug 145 for temporary fixation and alignment of the guide 120 with a prosthetic cup 150. The alignment plug 145 is a protrusion on the surface of the guide 120 formed to fit within a hole 155 of the guide 150. For example, as seen in FIG. 9, the guide 120 is placed within the prosthetic cup 150 and the plug 145 is in a hole 155 to form a plugged hole 157. Placement of the plug 145 aligns the one or more guide holes 140 with other holes 155 of the prosthetic cup 150 to form open holes 156. The plug 145 also provides temporary fixation of the guide 120 within the cup 150. The plug 145 engages a hole 155 and preferably forms a tight fit or friction fit within the hole 155. The engagement of plug 145 within hole 155 effectively provides a temporary fixed relationship between the plug 145 and hole 155 to prevent rotation of the guide 120 within the cup 150. In preferred embodiments, the end 143 of the plug 145 is flush with the outer surface 151 of the cup 150. In certain embodiments, the guide 120 includes a plurality of plugs 145.

Figure 10:
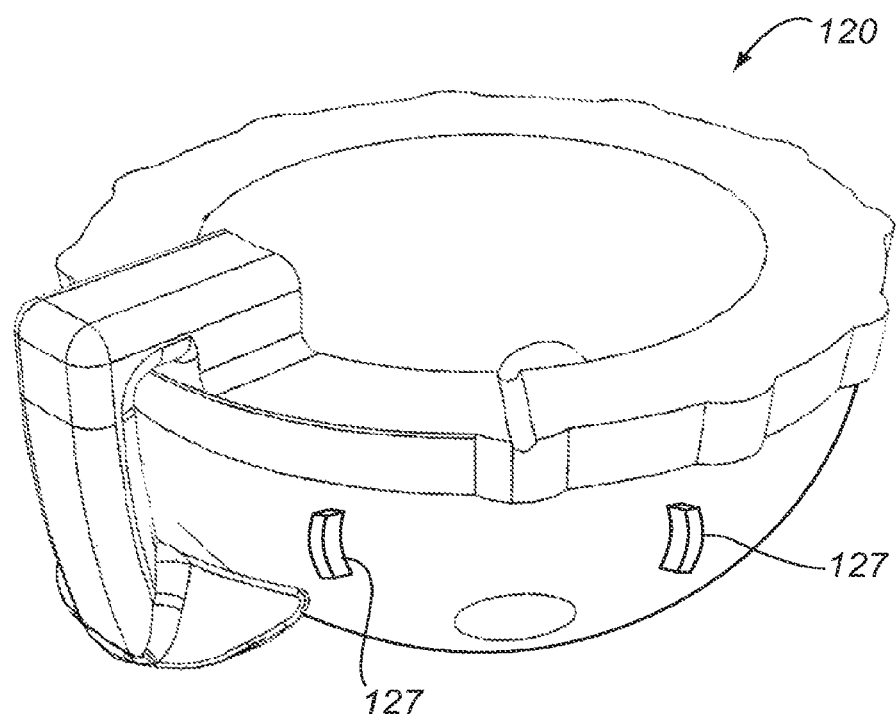
FIG. 10 depicts a guide with fins for temporary fixation with a prosthesis.
Figure 11:
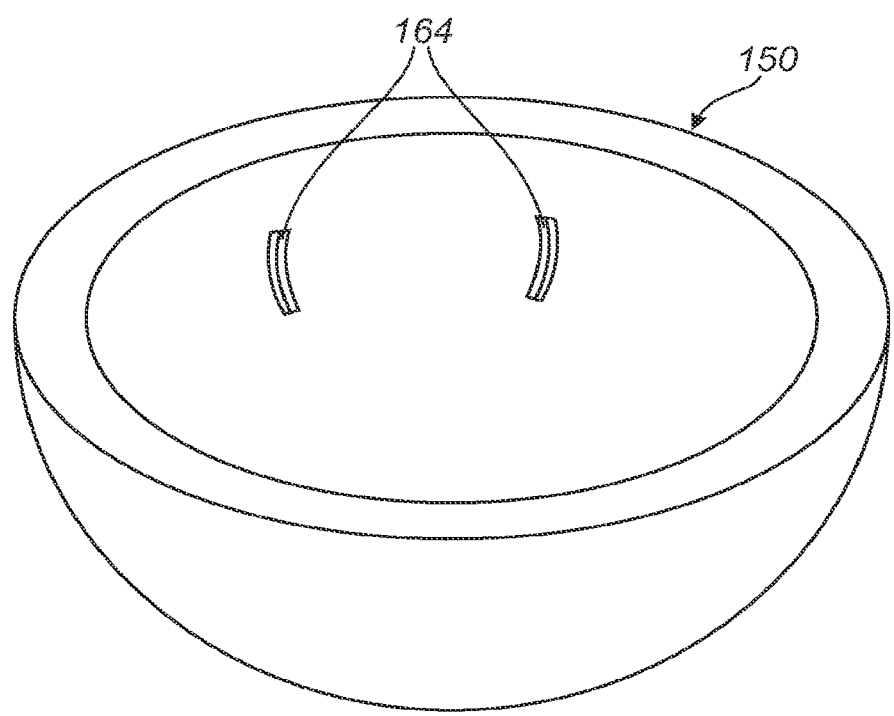
FIG. 11 depicts prosthesis with channels for temporary fixation with the guide of FIG. 10.

FIG. 10 shows a guide 120 with fins 127. The fins 127 may slide into channels of the prosthetic cup, for example, channels 164 of prosthetic cup 150 depicted in FIG. 11. The fins 127 are positioned on the guide 120 to correspond with the channels 164 of the cup 150 to align the guide holes 140 of the guide 120 with the holes 155 of the cup 150. When the guide 120 is placed into the cup 150, the fins 127 are slid into the channels 164, which, in turn, positions the guide 120 in a predetermined orientation to provide open holes 156. The fins 127 additionally provide temporary fixation of the guide 120 with the cup 150. For example, the fins 127 extend into and engage the channels 164, which prevents rotation of the guide 120 within the cup 150. Although the fins 127 and channels 164 are depicted as rectangular, the fins and channels may be other shapes, including, but not limited to, circular, ellipse, lozenge, cylindrical, navicular, oval, prolate, square, or triangle.

Figure 12:
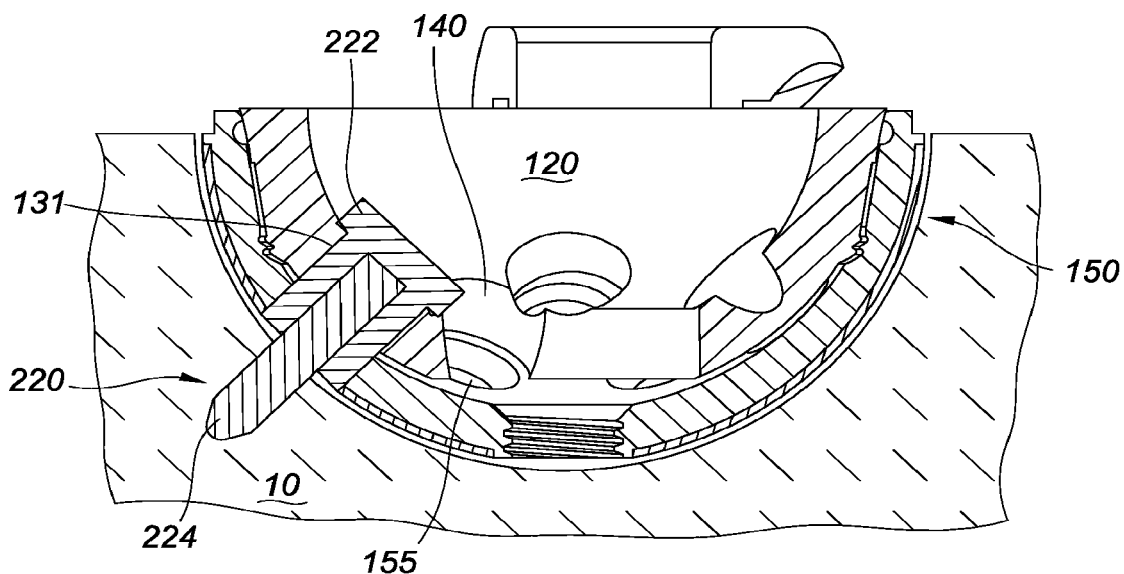
FIGS. 12-14 depict pin mechanisms for temporary fixation of a guide with a prosthesis.
Figure 13:
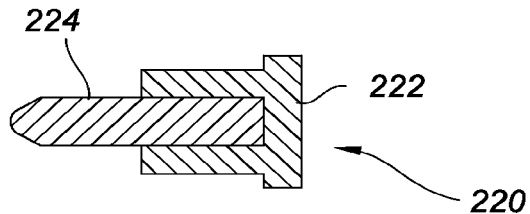

In certain embodiments, the guide and cup are locked with a pin. For example, the guide 120 depicted in FIG. 5 includes a locking pin hole 131. FIG. 12 shows a cross-sectional view of a guide 120 with a locking pin assembly 220 inserted into locking pin hole 131 to fix the guide 120 relative to the cup 150. The locking pin assembly 220 is inserted transversely through the guide 120 to prevent rotation or axial movement of the guide 120 relative to the prosthetic cup 150. The locking pin assembly 220 engages guide hole 140 and cup hole 155 to temporarily fix the relationship between the holes, and, in turn, the guide 120 and the cup 150. In certain embodiments, the locking pin assembly 220 forms a tight fit or friction fit within the open hole 156. The locking pin assembly 220 can also mate with the bone 10 to lock the prosthetic cup 150 relative to the bone 10 after disengaging the guide 120 from the prosthetic cup 150. In preferred embodiments, as depicted in FIG. 13, the pin assembly 220 includes an outer pin 222 for fixing the guide 120 relative to the cup 150, and an inner pin 224 for fixing the cup 150 to the bone 10. The outer pin 222 can be disengaged to remove the guide 120 while leaving the inner pin 224 engaged to the bone 10 to maintain the position of the prosthetic cup 150. In certain implementations, the outer pin 222 and the inner pin 224 are temporarily affixed to assist in inserting the pin assembly 220 as one piece. For example, the outer pin 222 and inner pin 224 may have threads or magnets. In alternative embodiments, a single pin, such as a cylindrical pin similar to inner pin 224, is used. The single pin has sufficient length to engage the guide, prosthesis, and bone. The guide 120 can be slid off the pin and away from the prosthetic cup 150, while the cup 150 remains fixed to the bone 10.

Figure 14:
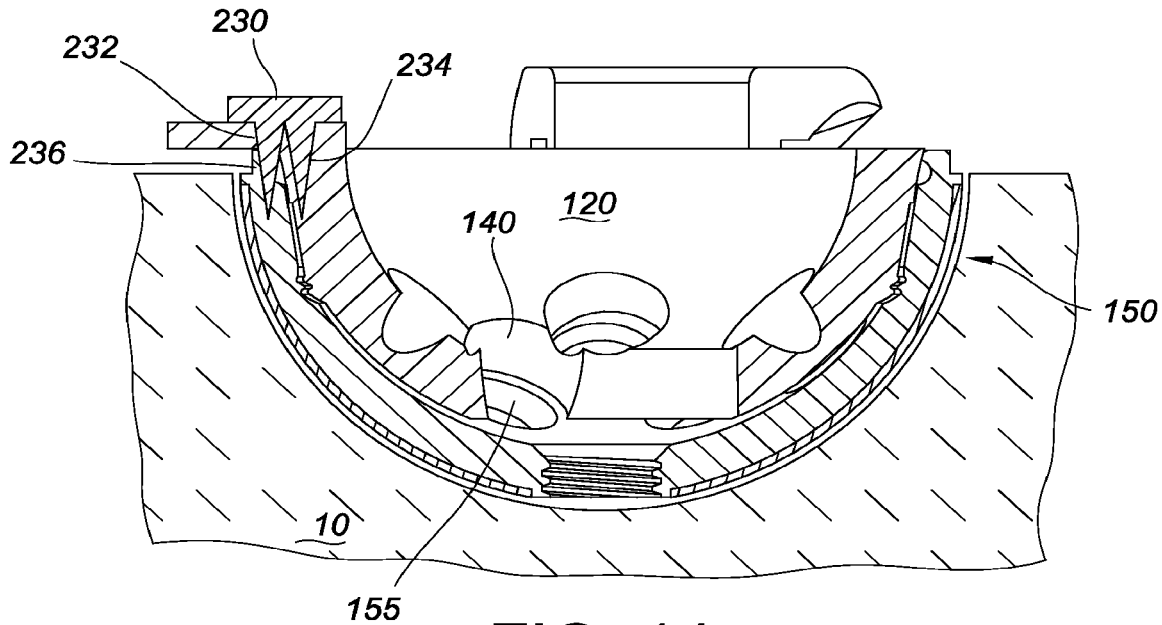

FIG. 14 illustrates a split pin 230 that locks the guide 120 with the prosthetic cup 150. For example, the guide 120 includes pin holes 232 and 234, while the cup 150 includes pin hole 236. In use, the guide 120 is positioned in the cup 150 so that the pin holes 232 and 236 are substantially aligned. The pin 230 is inserted into the pin holes 232, 234, and 236 to retain position of the guide 120 relative to the cup 150 with the holes 140, 155 properly aligned to form open holes 156. In certain embodiments, the split pin 230 is removable.

Combinations and subcombinations of the locking mechanisms may be used. For example, a guide and cup may be temporarily positioned with one or more of the locking mechanisms described herein. In alternative embodiments, the guide and the prosthetic cup are not locked together. The user holds the guide and cup in position while drilling fastener holes.

Figure 15:
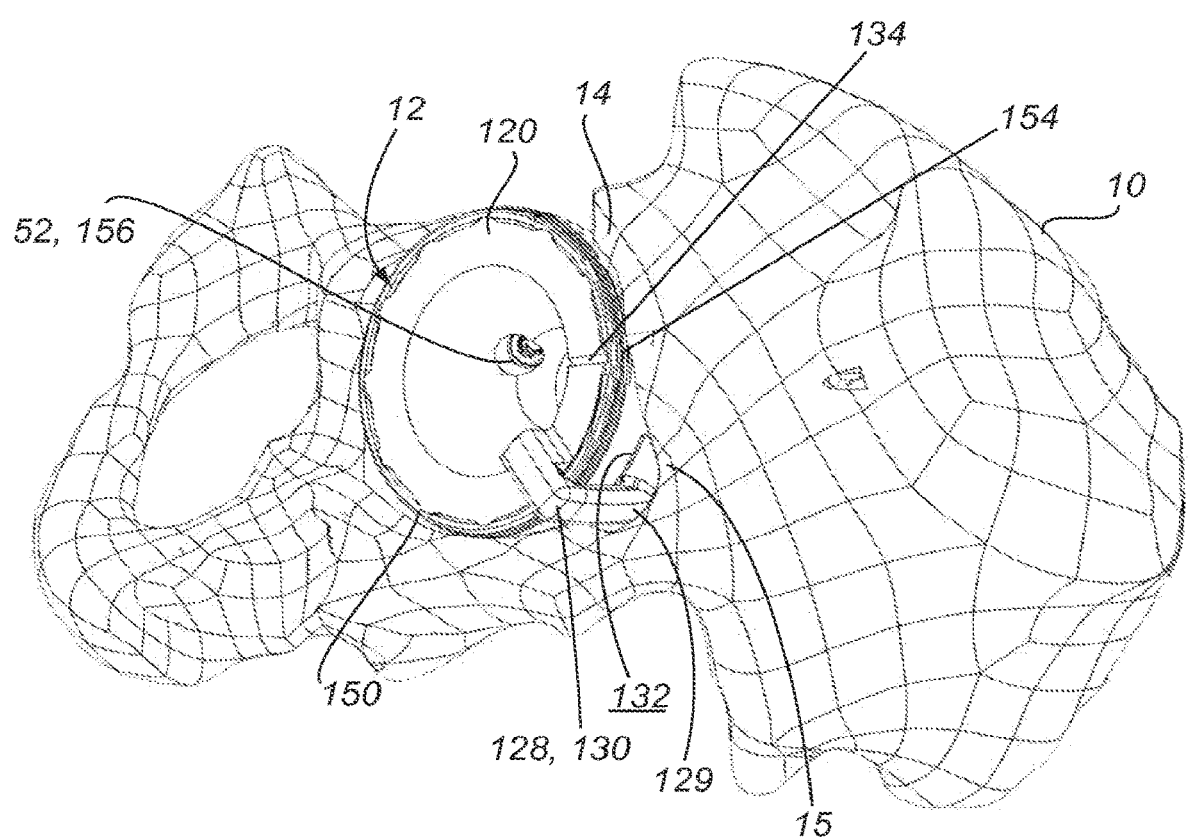
FIGS. 15 and 16 depict a guide and prosthesis placed at the acetabulum of a patient.
Figure 16:
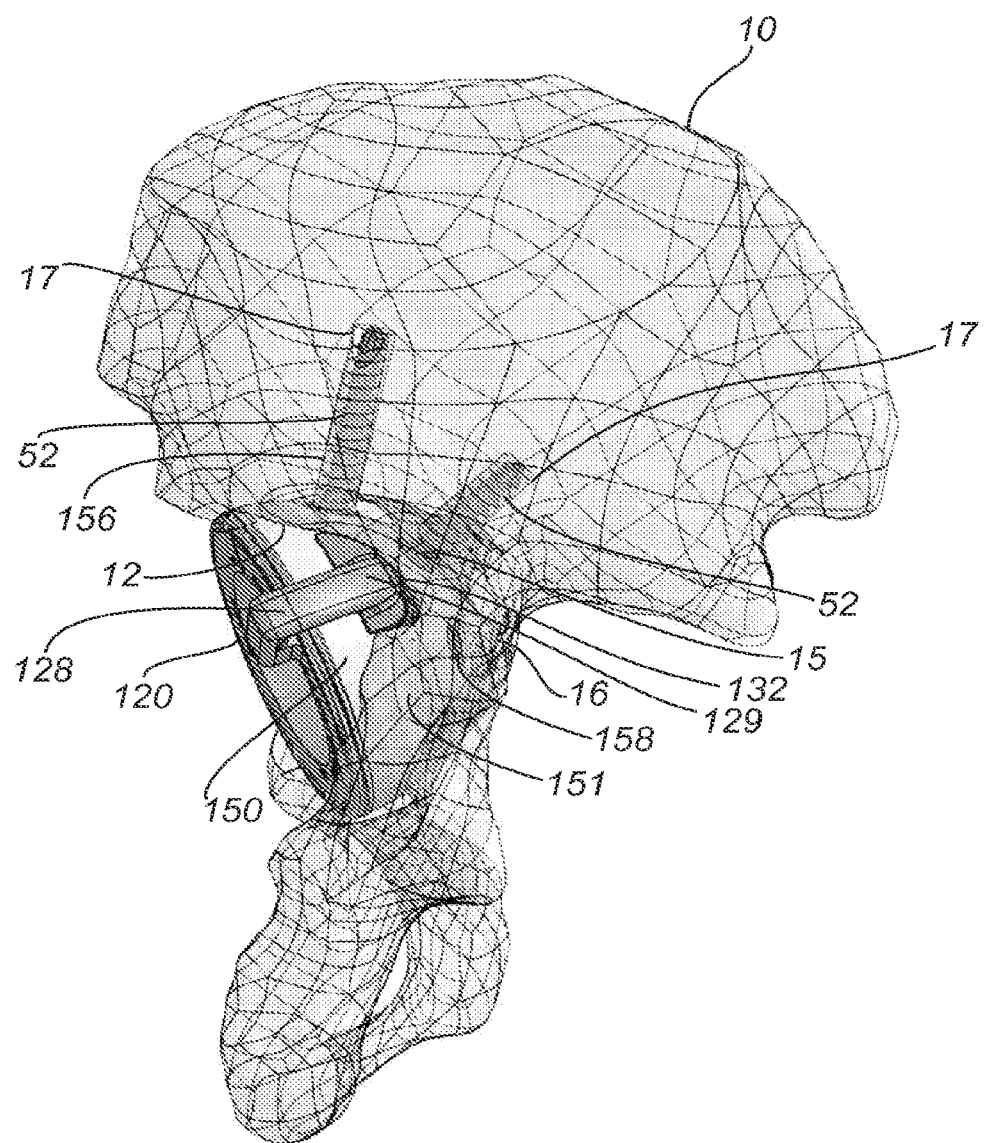

In practice, the cup 150 and guide 120 are inserted into the acetabulum 12 of a patient, as depicted in FIG. 15 and FIG. 16. The patient-matched surface 132 of the alignment structure 128 is coupled with a specific portion of the patient anatomy or anatomical alignment surface 15, as determined in a pre-operative plan based on patient data. The patient-matched surface 132 has a contour that is complementary to the anatomical alignment surface 15 of the patient's anatomy. Placement of the alignment structure 128 on the anatomical alignment surface 15 of patient's anatomy orients the guide 120 and cup 150, and aligns open holes 156 to expose those areas of the patient anatomy, such as portion 17, determined to be suitable for receiving a fastener, such as bone screw 52. The geometry of the patient-matched surface 132 substantially conforms to a particular portion of a patient's anatomy, such as patient alignment surface 15, in a single, unique position and orientation. For example, the patient-matched surface 132 may form a complementary fit with a notch or recessed area in the patient's anatomy. FIG. 15 and FIG. 16 show the patient-matched surface 132 contacting a recessed portion 15 of the acetabular rim 14 that is lower, relative to other portions of the rim 14, than the surrounding areas of anatomy.

The patient-matched surface 132 properly orients the guide 120 on the anatomy. In certain implementations, the patient-matched surface 132 is located on the arm 130 of the alignment structure 128. In certain embodiments, the entire end 129 of the arm 130 is configured as a patient-matched surface 132. In alternative embodiments, select portions of end 129 of arm 130 include a patient-matched surface 132. For example, the patient-matched surface 132 may be an extension from a portion of the end 129 of the arm 132. The patient-matched surface 132 may be textured to improve the stability of the guide 120 when placed on the patient's anatomy. For example, texturing can increase the friction between the patient-matched surface 132 and the bone surface 15 to prevent sliding of the guide 120 once the guide 120 is placed at the acetabulum 12. Examples of texturing that may be used to engage the patient-matched surface 132 with the patient surface 15 include, but are not limited to, serration, points, cross-hatch, grooves, ridges, bumps, or barbs.

The placement of the patient-matched surface 132 of the guide 120 also properly positions the cup 150 relative to the patient's anatomy, such as acetabulum 12. As shown in FIG. 15, when the guide 120 and cup 150 are inserted into the patient's acetabulum 12, the one or more open holes 156 expose the patient's anatomy 17 that has been determined to be suitable for receiving a fastener, such as screw 52. Areas of suitable anatomy are identified based on patient-specific data, as will below with regard to process 300. FIG. 16 shows a side view of the acetabulum 12 with the prosthetic cup 150 and guide 120 inserted therein, where fasteners 52 have been drilled into areas of suitable anatomy 17 and avoid areas of unsuitable anatomy 16. The outer surface 151 of the cup 150 couples with the acetabulum 12. The surgeon places screw 52 through the open hole 156 and into the suitable anatomy 17 of the acetabulum 12. In contrast, the covered holes 158, cannot receive a screw 52. The covered holes 158 correspond to areas unsuitable for receiving fastener, such as unsuitable area 16.

In certain embodiments, the placement of the patient-matched surface 132 at the patient's anatomy orients the cup with the proper abduction and anteversion (i.e., inclination and version) angles. For example, placement of the guide 120 may orient the cup 150 at an abduction angle of 45° and an anteversion angle of 20°. These angles are determined in the pre-operative plan based on patient-data.

After the implant 150 is properly aligned and secured, the alignment guide 120 is removed. Removal, which is relatively easy, is done by lifting the guide 120 out of the implant 150 after securing the implant 150 to the bone. Lifting the guide 120 from the secured implant 150 also releases temporary fixation mechanisms, such as those described in FIGS. 1-14. The guide 120 thus provides a patient-specific alignment and anchoring approach for the implant (e.g., the acetabular cup 150) and is also readily removable when the implant is seated and anchored. Moreover, the guide 120 can be used with standard, pre-formed implants, thus providing flexibility to the surgeon in implant selection.

In alternative embodiments, patient-matched drill guides similar to guide 120, are used independently of a prosthesis. For example, a patient matched drill guide may be provided having patient-matched surfaces to facilitate proper positioning and orientation with respect to a patient's anatomy to pre-drill holes before introducing the prosthesis into a surgical site.

In certain implementations, the cup portion 122 of the guide 120 serves as a trial feature for temporarily receiving a femoral head (which may be an implant or a trial) in order to evaluate correct positioning and orientation. In other embodiments, separate patient matched trials are designed using the systems and methods described herein.

Figure 17:
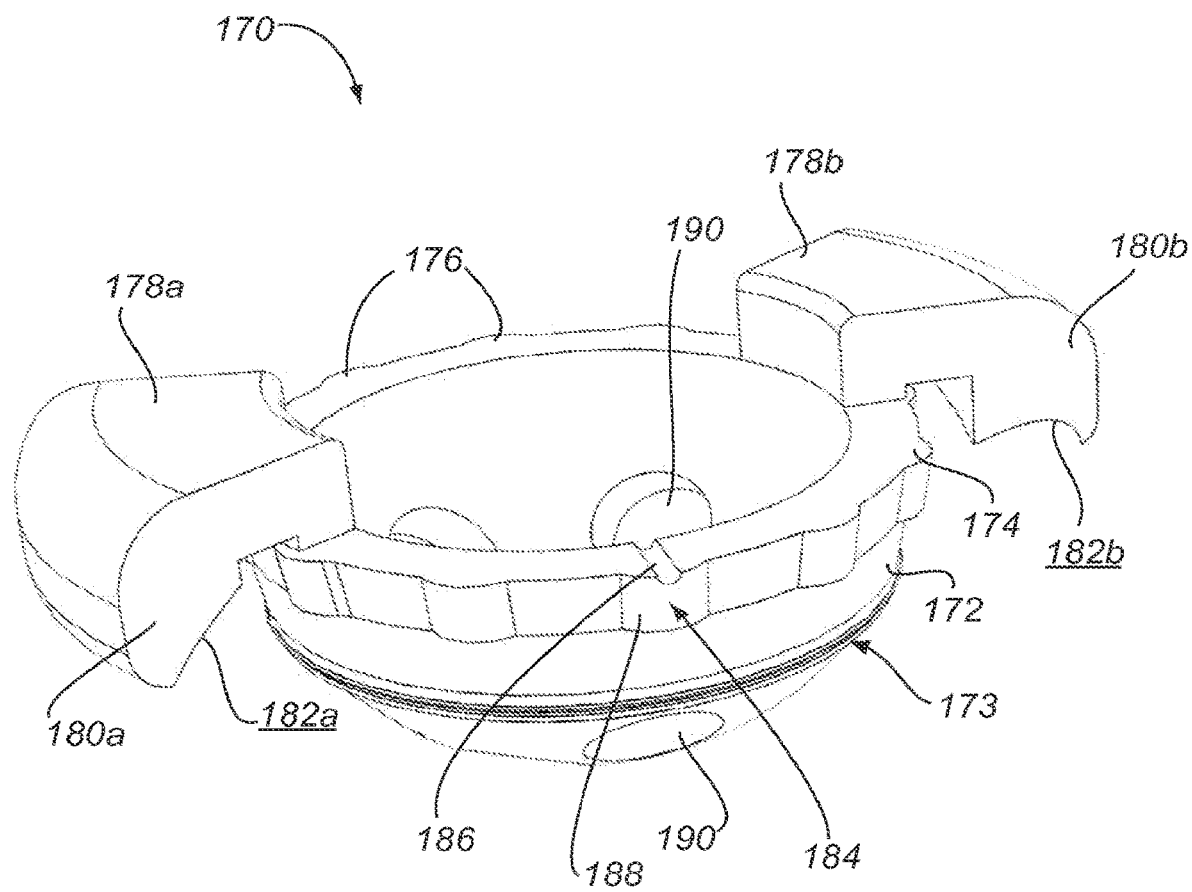
FIGS. 17-19 show an alternative embodiment of a surgical guide with a plurality of patient-matched alignment structures.
Figure 18:
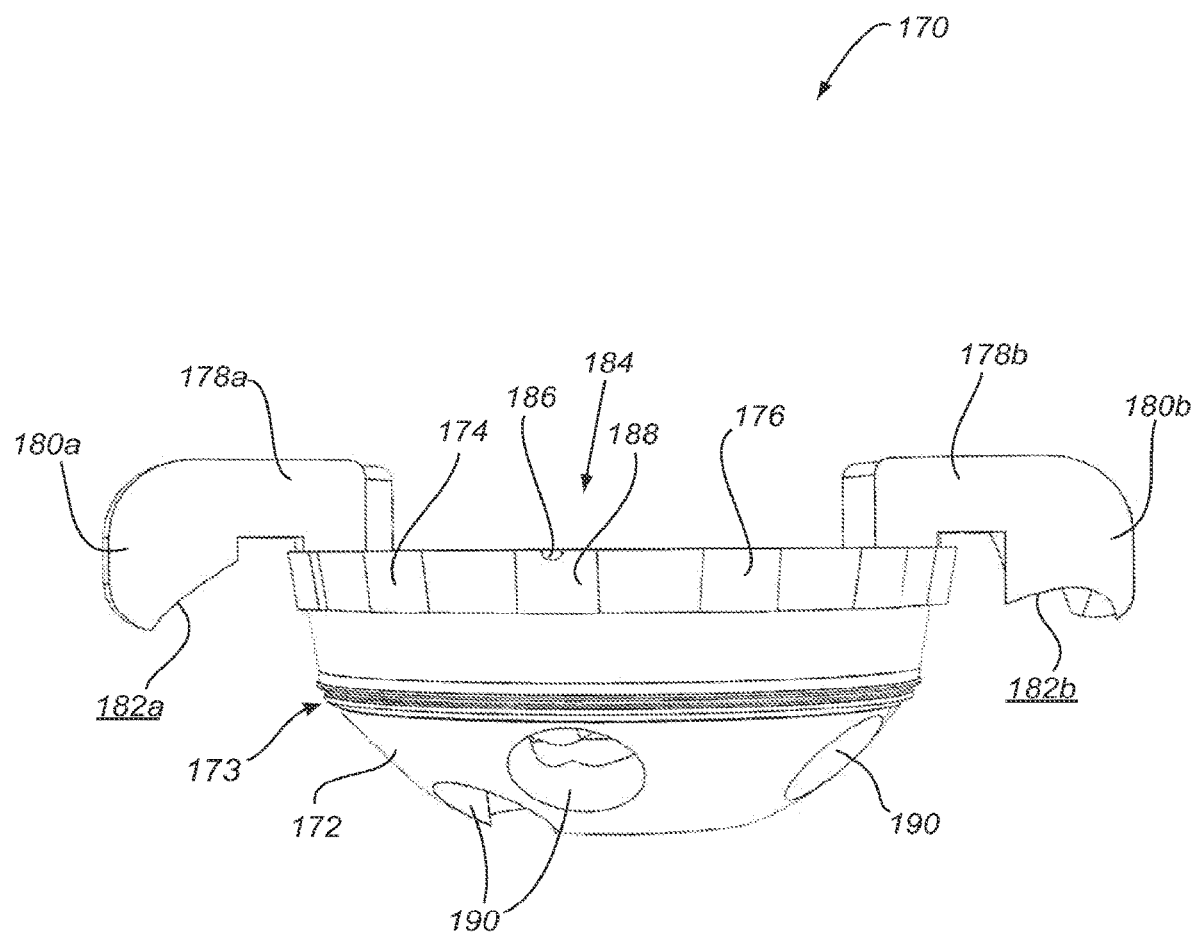
Figure 19:
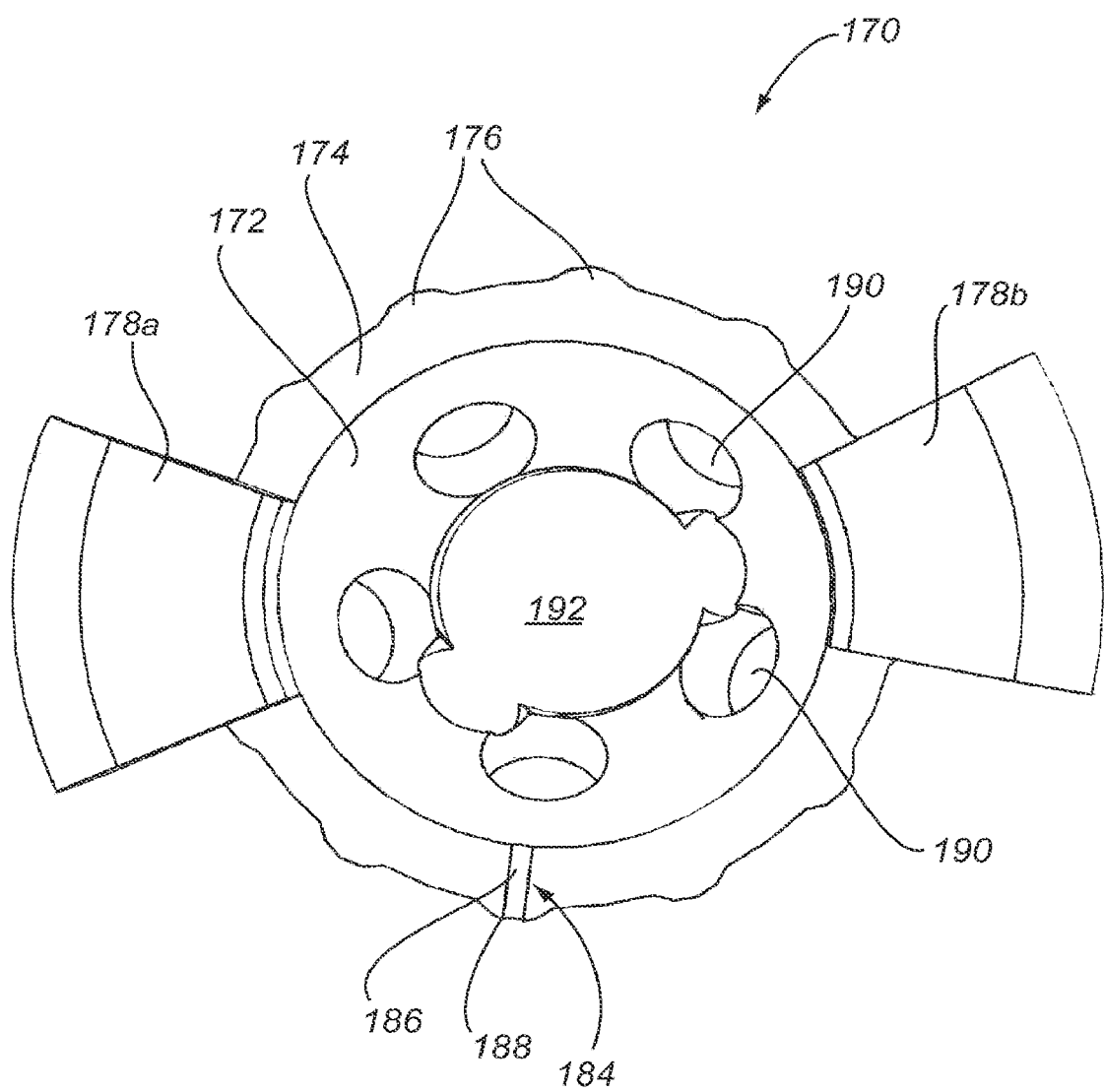

FIGS. 17-19 show an alternative embodiment of a surgical guide 170 with a plurality of patient-matched alignment structures 178. The general components of guide 170 are similar to those of guide 120. In the embodiment depicted FIGS. 17-19, guide 170 comprises a cup portion 172 and a rim portion 174. The cup portion 172 comprises at least one hole 190. In practice, the location and size of hole 190 is determined from patient-matched data and corresponds to areas of suitable anatomy within the patient's anatomy, similar to holes 140.

Figure 20:
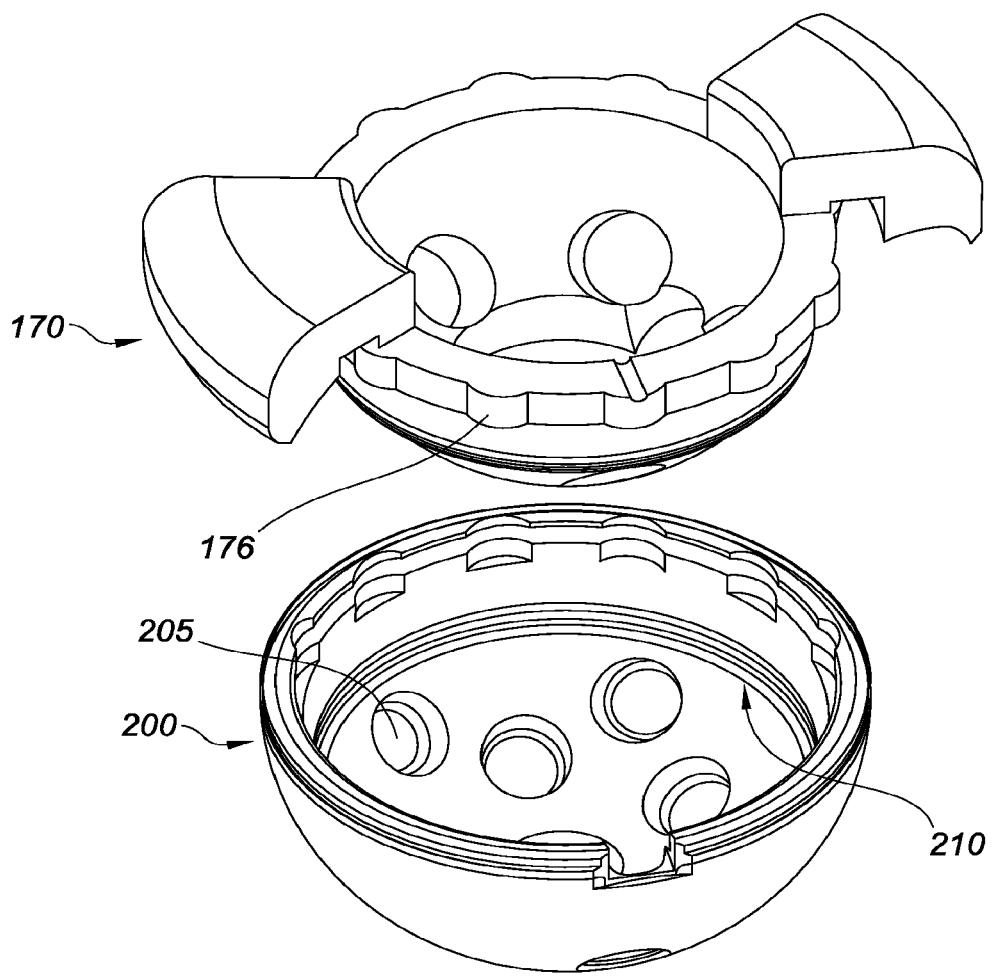
FIGS. 20-22 depict the guide of FIGS. 17-19 with a prosthesis.

FIG. 20 shows a prosthetic cup 200, similar to cup 150. The prosthetic cup 200 is a standard acetabular cup, for which the guide 170 provides customized placement, orientation, and fixation for a specific patient. In alternative embodiments, the prosthetic cup 200 is a customized device, having patient-contacting surfaces that are sized and shaped based on patient-matched data. The prosthetic cup 200 comprises holes 205, similar to holes 155. The location and size of the holes 155 may be standardized or patient-matched.

The guide 170 and cup 200 may be temporarily positioned and aligned using any of the previously described mechanisms, techniques, and features, including, but not limited to bumps, grooves, protrusions, dimples, keying structures, tapers, and pins. For example, as depicted in FIG. 20, the guide 170 includes one or more circumferential bumps 173 that seat in one or more circumferential grooves 210 of the prosthetic cup 200. In certain implementations, the guide 170 comprises protrusions 176 around the circumference of the rim portion 174 that are received within dimples 202 around the circumference of the prosthetic cup 200. In certain embodiments, the guide 170 has a prosthesis keying structure 184 that comprises a tongue 188 and a landmark identifier 186. The surgeon aligns the landmark identifier 186 with a corresponding keying structure 204 on the prosthetic cup 200 to position the guide 170 in the prosthetic cup 200. The holes 190 on the guide 170 align with the holes 205 on the prosthetic cup 200 to form open holes 206 over areas of suitable anatomy. The landmark identifier 186 may be a visual or tactile object, such as a slot, laser marking, indentation, or stamping. In the case of a tactile object, the landmark identifier may be a line, circular depression, square depression, triangular depression, or the like. In certain embodiments, the guide 170 comprises a central aperture 192 to create clearance for a surgical instrument, such as an impactor, to couple with the prosthetic cup 200.

The guide 170 includes a plurality of alignment structures 178 to orient the guide 170 with respect to the patient's anatomy. For example, as depicted in FIG. 19, the guide 170 includes two alignment structures 178a and 178b located opposite each other. A plurality of alignment structures 178 may be used to provide increased stability of the guide 170 when placed on the patient's anatomy. A plurality of alignment structures 178 may also be helpful to improve alignment if the patient's anatomy is particularly damaged, or if the anatomy is otherwise asymmetrical. In practice, each alignment structure 178a, 178b has an arm 180a, 180b and a patient-matched surface 182a, 182b on at least a portion of the overhang 180a, 180b. Each alignment structure 178, arm 180, and patient-matched surfaces 182 may have a different, unique shape. For example, as seen in FIG. 18 the patient-matched surface 182a on the left has a different shape than patient-matched surface 182b the right. In certain embodiments, the guide 170 includes three or more alignment structures 178.

Figure 21:
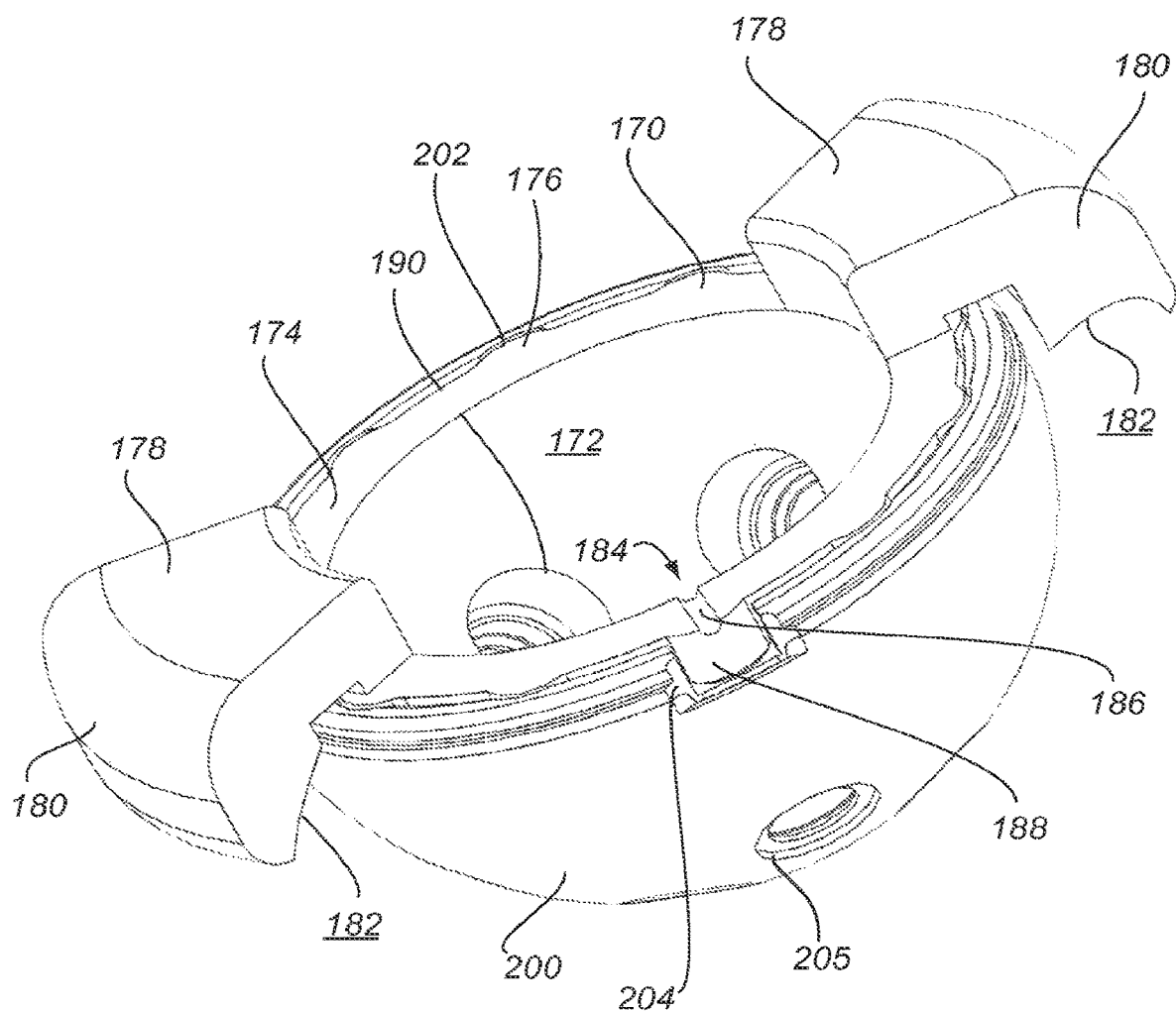
Figure 22:
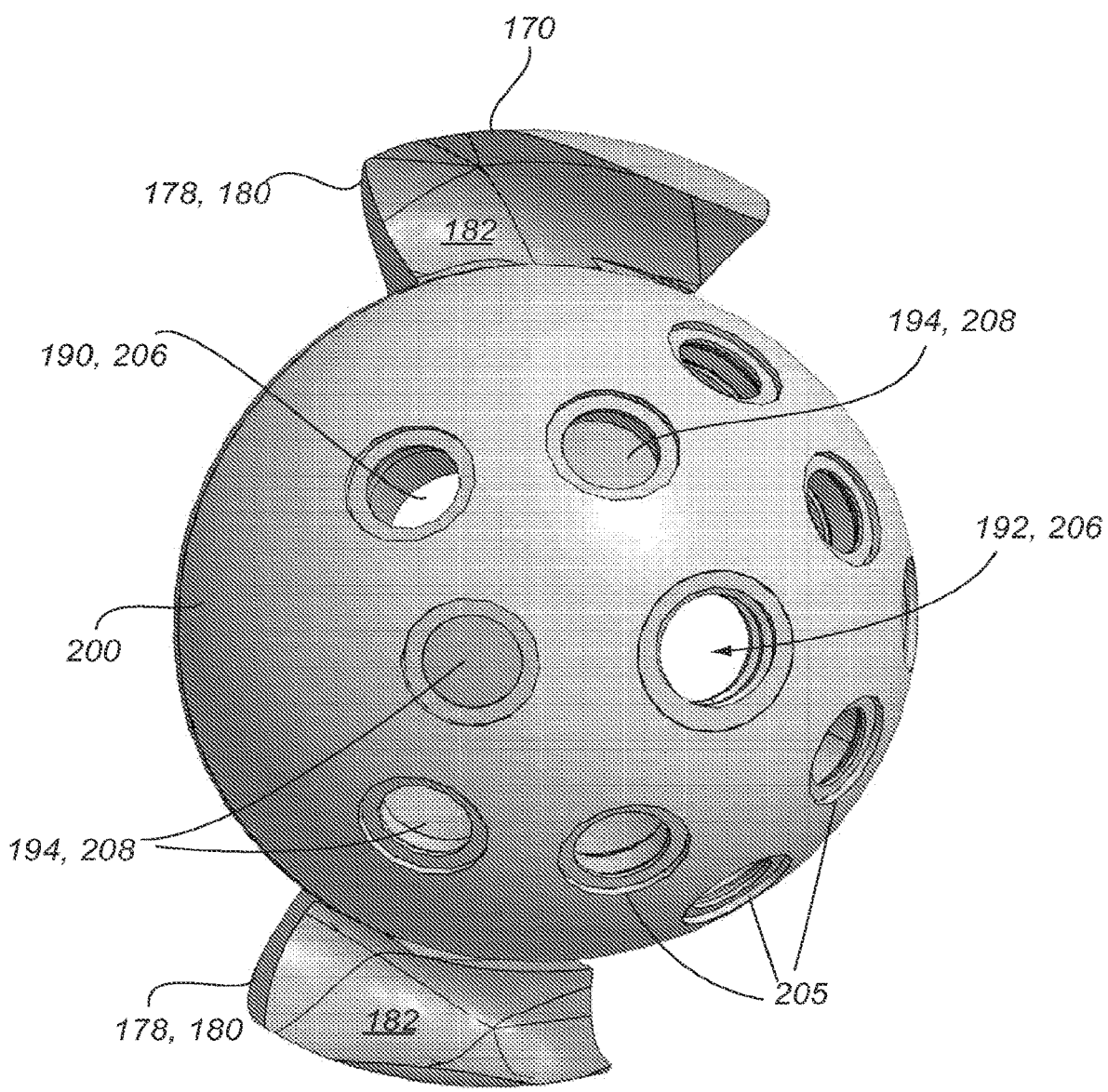

FIGS. 21-22 show the guide 170 positioned within the prosthetic cup 200. Similar to the placement of guide 120 within prosthetic cup 150, when the guide 170 is placed within the prosthetic cup 200, the hole 190 of the guide 170 aligns with a hole 205 of the prosthetic cup 200. This alignment provides open holes 206, which comprise a hole 205 of the prosthetic cup 200 and a hole 190 of the guide 170. FIG. 22 also shows covered holes 208 comprising a hole 205 of the prosthetic cup 200 that is covered by a solid portion 194 of the guide 170.

Figure 23:
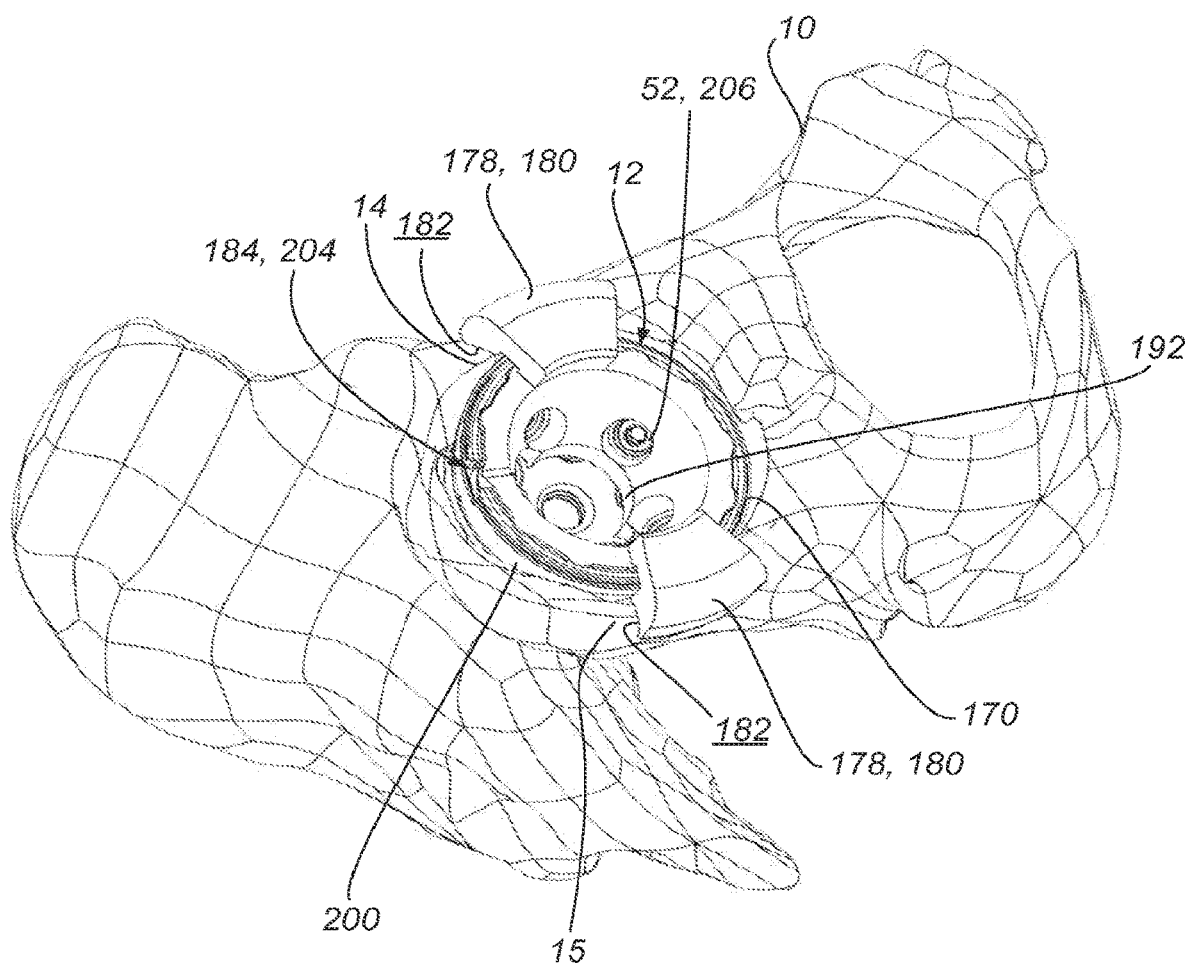
FIGS. 23 and 24 depict the guide and prosthesis of FIGS. 17-22 placed at the acetabulum of a patient.
Figure 24:
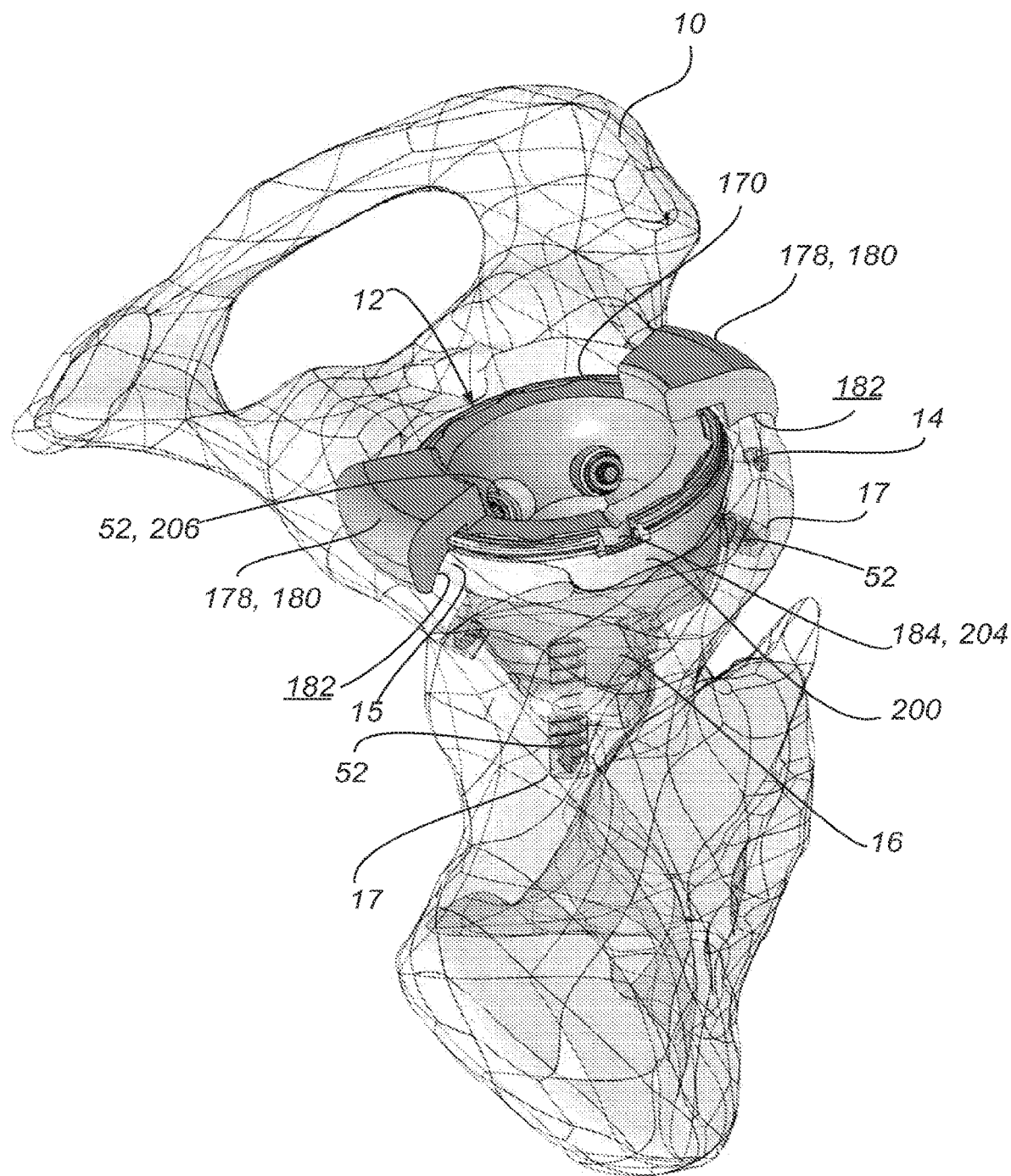

FIGS. 23-24 show a guide 170 and prosthetic cup 200 inserted into a patient's acetabulum 12. The patient-matched surfaces 182 contact an anatomical alignment surface 15 of the patient's acetabular rim 14 as determined in the pre-operative plan to ensure that the guide 120 is properly oriented on the anatomy. Each patient-matched surface 182 has a contour that is complementary to an anatomical alignment surface 15 of the patient's anatomy. Placement of the patient-matched surfaces 182 at the anatomical alignment surfaces 15 orients the one or more open holes 206 to expose areas 17 suitable for receiving a fastener. Open holes 206 guide drilling and placement of a fastener, such as bone screw 52, such that the screw 52 is placed within an area of suitable anatomy 17, as determined in the pre-operative plan based on patient data. On the other hand, covered holes 208 prevent drilling or otherwise using a fastener at those locations.

Figure 25:
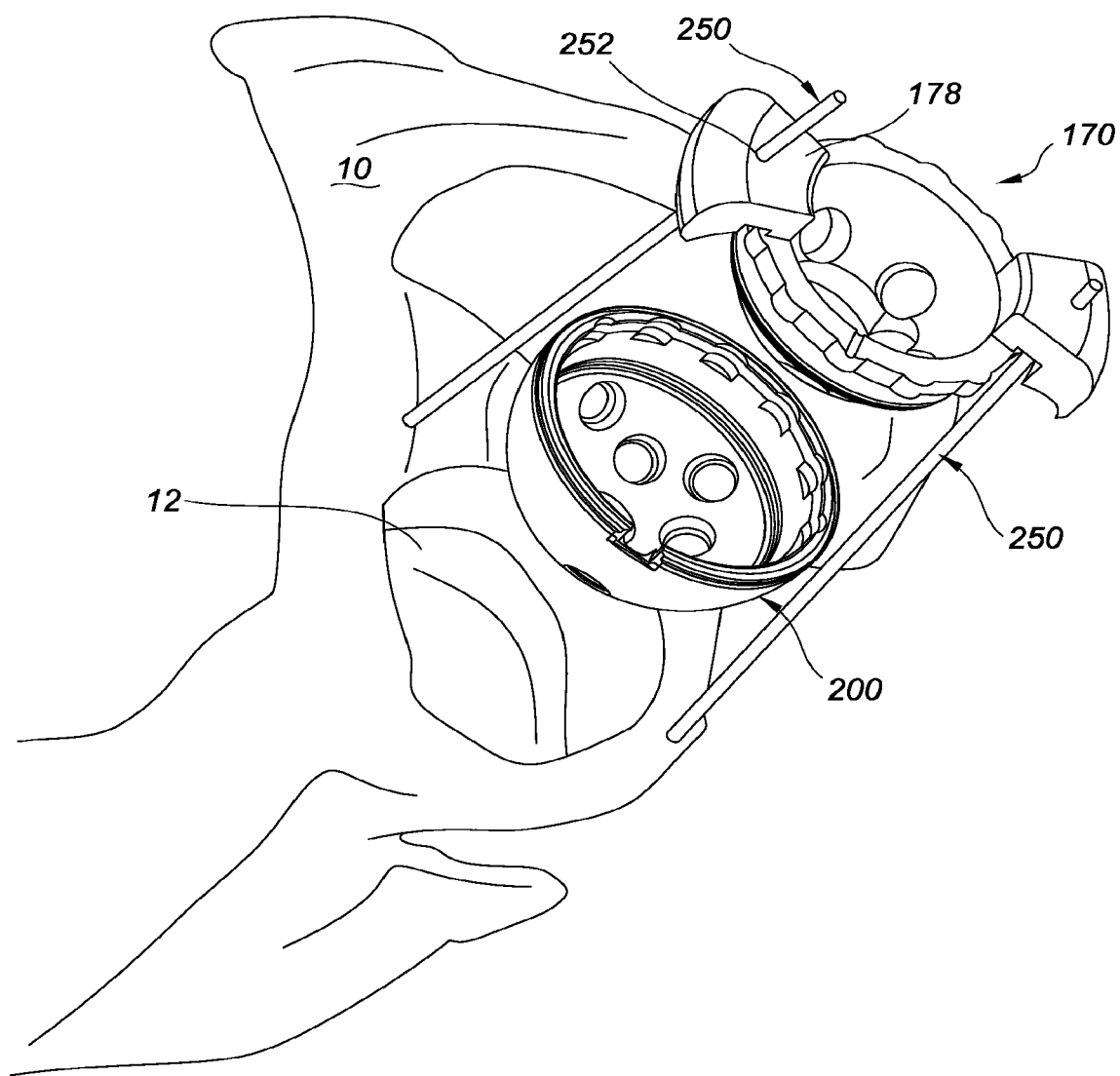
FIG. 25 shows an embodiment of a guide fixed relative to the patient's bone.

FIG. 25 illustrates an alternative embodiment for temporary fixation of the guide 170 using pins 250 affixed to the bone 10. In certain implementations, each alignment structure 178 includes at least one aperture 252. The pins 250 are placed within the aperture 252 and coupled to the bone 10. In certain embodiments, the apertures 252 are used to pre-drill holes into the bone for placement of pins 250 or other fasteners. The prosthetic cup 200 is coupled to the guide 170, as previously described, before placing the guide 170 and cup 200 into the acetabulum 12. The pins 250 prevent axial and rotational motion of the guide 170, but allow the guide to slide down along the pins 250 for placement of the prosthetic cup 200 into the acetabulum 12. The pins 250 could also be used with guide 120.

Various method steps may be performed to create the devices having patient-matched features described herein. In practice, imaging data of the patient's anatomy is acquired and the data is used to determine areas of anatomy suitable for receiving a fastener, develop a plan before the surgery for placing a prosthetic cup and inserting fasteners ("pre-operative plan"), and design a customized, patient-matched guide for placing the cup and fasteners according to the pre-operative plan. The guide is then manufactured and used for the specific patient to place the prosthetic cup and fasteners.

Figure 26:
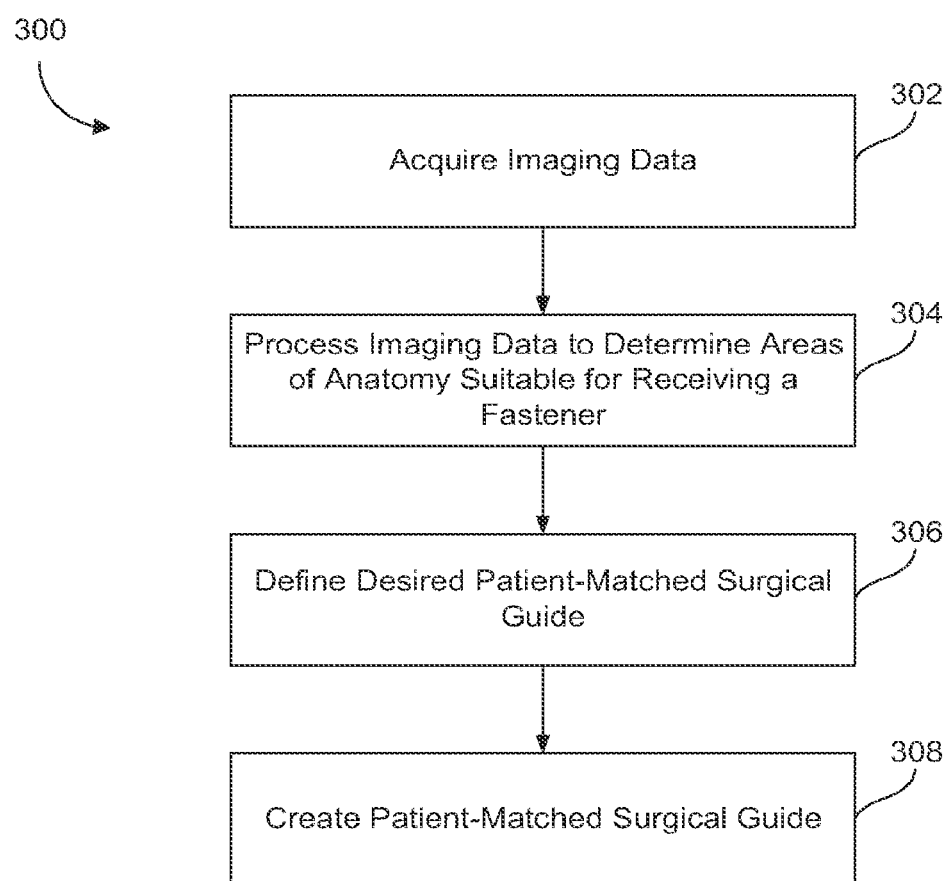
FIG. 26 illustrates a method of making a surgical guide with a patient-matched alignment structure.

FIG. 26 shows a method 300 for developing a pre-operative plan and creating patient-matched devices, such as guide 120 and guide 170. The term patient-matched device refers generally to any of the devices described herein having patient-matched features. Method 300 includes a step 302 of acquiring imaging data about the geometry of the specific patient's anatomy. For example, imaging data may include, but is not limited to, data about the bone, cartilage, or other anatomy of interest, data sufficient to determine relevant mechanical properties and axes, data regarding the amounts and locations of unsuitable anatomy, data regarding the topography of the anatomy, and data regarding the amounts and locations of suitable anatomy that may be of sufficient quality to accept a mechanical fastener. The imaging data may be obtained with magnetic resonance imaging, X-ray (including, but not limited to digital X-rays and X-ray absorptiometry for determining bone density), ultrasound, computed tomography (CT), or other techniques. For ease of reference, the systems and methods described herein refer generally to "imaging data," although it should be understood that in other embodiments, non-image based technologies could be used to obtain sufficient data about the anatomy of interest. In some embodiments, the imaging data does not relate to the entire portion of the anatomy of interest (e.g., the entire acetabulum), but instead, relates only to certain key or desired anatomical points or areas (e.g., the medial portion of the acetabulum).

The imaging data is then processed to define areas of anatomy suitable for receiving a fastener at step 304 of method 300. The processed imaging data provides the surgeon, technician, or other user with a clear view of the most relevant anatomical features. In certain embodiments the imaging data may be processed to remove images or portions thereof that correspond to areas of the anatomy that are not of interest during the surgery. For example, images of soft tissue may be removed if they obscure other portions of the anatomy that will be of interest, such as the bony anatomy. Step 304 may include processing the imaging data to create a three-dimensional model of the patient's anatomy.

Bone density can serve as a measure of bone quality. In certain forms of imaging data, bone density is proportional to the color density. For example, a higher density image can be indicative of a higher density bone region and suitable areas may show up as sufficiently high density on the imaging data. When judging bone thickness, a user may identify areas that are thick enough to receive the fastener. Generally speaking, a fastener will have better attachment to the bone with the greater number of threads that are passing through the bone. Therefore, the user may align fasteners to be inserted into regions of bone that are thick enough to engage the greatest number of threads on the fastener. Additionally, determining areas of suitable anatomy may include identifying areas that should be avoided, such as blood vessels and nerves. Certain locations may be generally preferable for a fastener. For example, the densest bone in the pelvis is typically located superiorly towards the iliac crest following a posterior thickened ridge, and is a preferred location for screw placement when available.

The patient-matched device is defined and designed at step 306 of method 300. In certain embodiments, step 306 comprises multiple sub-steps. For example, step 306 may include identifying a desired position, orientation, or depth of instruments or implants with respect to the patient's anatomy to develop a pre-operative plan based on patient data. Step 306 may also include designating alignment axes, cutting planes, or other constructs or references. In certain embodiments, step 306 includes determining a portion of the patient anatomy, or anatomical alignment surface, for placement of the patient-matched structure, such as alignment structures 128 and 178. In certain embodiments, step 306 includes determining the shape of a patient-matched surface, such as surfaces 132 or 182, for an alignment structure, such that the patient-matched surface has a contour complementary to a selected portion or alignment surface of the patient's anatomy. In certain embodiments, step 306 includes determining the target position of an acetabular cup, for example, by defining target abduction and anteversion angles. For example, the target orientation of the cup may be a 45° abduction angle and a 20° anteversion angle. In some embodiments, the patient-matched device is automatically or semi-automatically defined based on the three-dimensional model, the designated reference data, and other inputs, such as a blank from which the patient-matched device is defined.

The location of the holes of the guide may be determined based the areas of suitable anatomy determined in step 304. Specifically, the guide holes are positioned to correspond to the patient's suitable anatomy that is of sufficient quality to accept mechanical fasteners. Additionally, determining the location, position, and orientation of holes and related fasteners may include avoiding sensitive areas such as blood vessels and nerves. The imaging data may provide relevant data to determine unsuitable areas, which should be avoided, as discussed with step 304. Avoidance of critical anatomical features may be accomplished through a user's general surgical and anatomical knowledge. In certain embodiments, determining unsuitable areas to avoid is accomplished in an automated fashion by defining rules of proximity to ensure that fasteners or screws are not spaced too closely. In certain embodiments, no holes are included on the guide. In certain approaches, the holes may not be necessary because the prosthesis or cup may be secured to the patient anatomy without screws. For example, the cup may be secured by a tight fit with thee acetabulum or with bone cement, or the surgeon may decide to place screws without the guide.

There may be any number of holes provided on the prosthesis and the holes may be in any location corresponding to suitable anatomy. In certain embodiments the prosthesis implant is a customized, patient-matched implant. Additionally, patient-matched data can be used to determine the size and other properties of holes and/or fasteners. For example, patient-matched data may be used to determine an appropriately sized fastener to use, and accordingly, an appropriately sized hole in the guide or prosthesis. For example, if there is a particularly large or deep area of suitable anatomy in one location, a larger fastener and a larger hole may be desired for improved fixation. In certain implementations, patient-matched data may be used to determine an appropriate fastener length. In certain implementations, patient-matched data may be used to determine an appropriate fastener type, such as a cortical screw, a cancellous screw, or an osteopenic screw. In certain embodiments, the holes and/or fasteners may be configured to provide for locking of the fastener in the hole in order to increase rigidity of the construct. Such locking features may include, but are not limited to, threads in the hole or on the head of the fastener, deformable materials, geometries creating an interference fit between the fastener and the hole, and any other methodology, mechanism, or structure for locking the fastener in the hole at a fixed angle.

Determining location, position, or orientation of holes and related fasteners may be a manual process or automated. In the case of manual determination, a user makes decisions based on each patient by considering factors such as bone density, thickness, and anatomical structure. For example, a 75-year-old female typically has a different scale of bone density than a 35-year-old male. The user looks at the patient's imaging data as a whole and makes decisions that are an appropriate fit considering all parameters for that patient. Certain locations are generally preferred for fastener placement. For example, the densest bone in the pelvis is typically located superiorly towards the iliac crest following a posterior thickened ridge, and is a preferred location for screw placement when available. In certain embodiments, rules may be applied, to maintain a particular distance (e.g., 10 mm) from areas of concern, (e.g., blood vessel, nerve, or low bone quality).

In some embodiments, one or more of the above described steps could be performed using stand-alone or networked computer equipment. Such computer equipment, in some embodiments, could include memory, a processor, and input/output features, which facilitate performing at least some of the above identified steps, including creating one or more models. One or more of the above described steps could be performed using a computer assisted design (CAD) software package or other types of design software packages.

If desired, the proposed patient-matched device may be shown to the surgeon, who may suggest changes or alterations to the proposed device. For example, the surgeon could decide to eliminate certain structure (e.g., holes or keying features) or add other structures.

The method 300 includes step 308 for creating or manufacturing the patient-matched device. Several methods or technologies can be used to manufacture the device, including, but not limited to, traditional manufacturing technologies (i.e., a lathe or other milling process, molding processes, sintering of porous surfaces, plasma spraying, etc.), rapid production technologies (i.e., three-dimensional printing or selective laser sintering), or a combination of the two.

The foregoing is merely illustrative of the principles of the disclosure, and the systems, devices, and methods can be practiced by other than the described embodiments, which are presented for purposes of illustration and not of limitation. As various modifications could be made to the exemplary embodiments, without departing from the scope of the inventions described herein. Thus, the breadth and scope of the invention should not be limited by any of the above-described exemplary embodiments.

It is to be understood that the systems, devices, and methods disclosed herein, while shown for use in knee systems, may be applied to systems, devices, and methods to be used in other surgical procedures including, but not limited to, spine arthroplasty, cranio-maxillofacial surgical procedures, hip arthroplasty, shoulder arthroplasty, as well as foot, ankle, hand, and extremities procedures.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A computer-implemented method comprising:
   acquiring patient data related to an anatomy of a patient, wherein at least some of the patient data comprises imaging data;
   processing the imaging data to identify one or more locations of the anatomy suitable for receiving a fastener;
   determining a target implant position and orientation based on the patient data and one or more required implant characteristics; and
   generating a pre-operative surgical plan for introducing a prosthetic implant based on the one or more locations and the target implant position and orientation, wherein the pre-operative surgical plan relates to at least one patient-matched surface.

2. The method of claim 1, wherein the patient data is related to a geometry of a bony anatomy, a geometry of soft tissue, a mechanical property of the anatomy, a mechanical axis of the anatomy, a topography of the anatomy, or a combination thereof.

3. The method of claim 1, wherein the patient data relates to at least a portion of an acetabulum of the patient, and wherein the prosthetic implant is an acetabular cup.

4. The method of claim 1, wherein processing the imaging data comprises calculating a color density at each of a plurality of locations of the anatomy, wherein the color density is indicative of a bone density.

5. The method of claim 3, wherein processing the imaging data further comprises identifying, based on the patient data and the bone density, the one or more locations from the plurality of locations.

6. The method of claim 1, wherein a bone thickness at each of the one or more locations meets a predetermined threshold bone thickness.

7. The method of claim 1, wherein generating a pre-operative surgical plan comprises defining, based on the patient data, a patient-matched prosthetic implant having each of the one or more required implant characteristics.

8. The method of claim 1, wherein the one or more required implant characteristics includes one or more fastener hole positions.

9. The method of claim 8, wherein, when placed in the target implant position and orientation, each of the one or more fastener hole positions of the prosthetic implant is aligned with one of the one or more locations.

10. The method of claim 1, wherein processing the imaging data further comprises identifying at least one alignment surface on the anatomy.

11. The method of claim 10, wherein the at least one patient- matched surface is complementary to the at least one alignment surface.

12. The method of claim 1, wherein the target implant position and orientation comprises a target abduction angle, a target anteversion angle, or a combination thereof.

13. The method of claim 1, wherein the pre-operative surgical plan comprises a fastener size, a fastener length, or a combination thereof.

14. The method of claim 1, wherein the pre-operative surgical plan comprises one or more selected fasteners.

15. The method of claim 14, wherein the one or more selected fasteners comprise a cortical screw, a cancellous screw, an osteopenic screw, or a combination thereof.

16. The method of claim 1, wherein the data is related to one or more sensitive areas in the anatomy of the patient, and wherein the one or more locations are at least a predetermined distance from each of the one or more sensitive areas.

17. The method of claim 16, wherein the one or more sensitive areas comprise an area proximate to a nerve, an area proximate to a vessel, an area of low bone quality, or a combination thereof.

18. A system for generating a pre-operative surgical plan, the system comprising: a processor; and a non-transitory, processor-readable storage medium that stores instructions executable by the processor to: acquire patient data related to an anatomy of a patient, wherein at least some of the patient data comprises imaging data, process the imaging data to identify one or more locations of the anatomy suitable for receiving a fastener, determine a target implant position and orientation based on the patient data and one or more required implant characteristics, and generate a pre-operative surgical plan for implanting a prosthetic implant based on the one or more locations and the target implant position and orientation, wherein the pre-operative surgical plan relates to at least one patient-matched surface.

* * * * *